(12) United States Patent
Marat et al.

(10) Patent No.: US 8,530,511 B2
(45) Date of Patent: Sep. 10, 2013

(54) ADMINISTRATION OF DITHIOLANE COMPOUNDS FOR PHOTOPROTECTING THE SKIN

(75) Inventors: Xavier Marat, Paris (FR); Karine Lucet-Levannier, Ruell-Malmalson (FR); Laurent Marrot, Livry Gargan (FR)

(73) Assignee: L'Oreal, Paris (FR)

( * ) Notice: Subject to any disclaimer, the term of this patent is extended or adjusted under 35 U.S.C. 154(b) by 730 days.

(21) Appl. No.: 12/585,785

(22) Filed: Sep. 24, 2009

(65) Prior Publication Data

US 2010/0197759 A1    Aug. 5, 2010

Related U.S. Application Data

(60) Provisional application No. 61/202,085, filed on Jan. 28, 2009, provisional application No. 61/136,755, filed on Sep. 30, 2008.

(30) Foreign Application Priority Data

Sep. 24, 2008  (FR) ..................................... 08 56414
Nov. 28, 2008  (FR) ..................................... 08 58078

(51) Int. Cl.
*A01N 43/26* (2006.01)
*A61K 31/385* (2006.01)
*C07D 339/02* (2006.01)
*C07D 341/00* (2006.01)
*C07D 409/00* (2006.01)

(52) U.S. Cl.
USPC ........................................... 514/440; 549/35

(58) Field of Classification Search
USPC .......................................... 514/440; 549/35
See application file for complete search history.

(56) References Cited

U.S. PATENT DOCUMENTS 6,313,164 B1 * 11/2001 Fujita et al. .................. 514/440

FOREIGN PATENT DOCUMENTS

| EP | 0 869 126 A1 | 10/1998 |
| JP | 2000-169371 A | 6/2000 |
| JP | 2006206513 A * | 8/2006 |
| WO | WO 9823606 A1 * | 6/1998 |
| WO | WO 2008/058999 A1 | 5/2008 |

OTHER PUBLICATIONS de Gruijl et. al. Journal of Photochemistry and Photobiology B: Biology, 2001, Elsevier, vol. 63, pp. 19-27.*
Sinha et. al., Photochemistry and Photobiological Sciences, 2002, The Royal Society of Chemistry and Owner Societies, vol. 1, pp. 225-236.*
Spiteller, Experimental Gerontology, 2001, Elsevier, vol. 36, pp. 1425-1457.*
http://www.merriam-webster.com/dictionary/prevent.*
Vippagunta et. al., Advanced Drug Delivery Reviews, 2001, Elsevier, vol. 48, pp. 3-26.*
Hussain et. al., Nature Reviews Cancer, 2003, Nature Publishing Group, vol. 3, pp. 276-285.*
XP-002524712; Kogyo et al., "Preparation and formulation of cyclic dithio derivatives as remedies for diabetic kidney diseases. Hypoglycemic agents, hypolipidemic agents, and lenitives for digestive disorders" Chemical Abstract Service, Oct. 7, 1998, Columbus, Ohio, Database Accession No. 1998:388511.

* cited by examiner

*Primary Examiner* — Sreeni Padmanabhan
*Assistant Examiner* — Sarah Pihonak
(74) *Attorney, Agent, or Firm* — Buchanan Ingersoll & Rooney PC

(57) ABSTRACT

Dithiolane compounds having the structural formula (I):

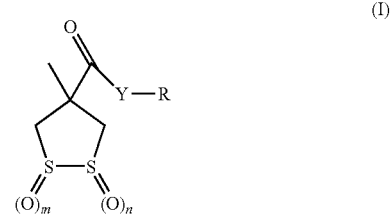

are useful for reinforcing and/or preserving the natural antioxidant protection of the skin against oxidative stress caused, especially, by UV radiation, e.g., by increasing the level of intracellular glutathione.

19 Claims, 3 Drawing Sheets

ADMINISTRATION OF DITHIOLANE COMPOUNDS FOR PHOTOPROTECTING THE SKIN

CROSS-REFERENCE TO PRIORITY/PROVISIONAL APPLICATIONS

This application claims priority under 35 U.S.C. §§119 and 120 of FR 0856414, filed Sep. 24, 2008; FR 0858078, filed Nov. 28, 2008, and of U.S. Provisional Applications Nos. 61/202,085, filed Jan. 28, 2009, and 61/136,755, filed Sep. 30, 2008, each hereby expressly incorporated by reference and each assigned to the assignee hereof.

BACKGROUND OF THE INVENTION

1. Technical Field of the Invention

The present invention relates to the administration of particular dithiolane compounds of formula (I) in compositions that are useful in the field of treating or preventing disorders of the skin induced by oxidative stress, especially caused by solar radiation, and to compositions containing them.

2. Description of Background and/or Related and/or Prior Art

The skin is the outermost organ of the body and is thus the first target for environmental stress factors, most particularly represented by the ultraviolet radiation of sunlight, UV-B and UV-A. Specifically, acute or chronic exposure to sunlight is known to induce deleterious biological and clinical effects on the body.

Skin damage caused by chronic exposure (repeated irradiation) or acute exposure (strong irradiation) to UV-A or UV-B has been extensively studied; it is especially known that:

UV-B rays (290-300 nm; 5% of the total UV), which have the most energetic wavelengths, most especially affect the epidermal cells (keratinocytes), by acting on DNA;

UV-A rays (320-400 nm; 95% of the total UV), which penetrate more deeply, reach the dermal cells such as the fibroblasts and act indirectly via the generation of free radicals;

furthermore, prolonged exposure to ultraviolet radiation has the effect of stimulating the expression of collagenases, particularly type 1 matrix metalloprotease (MMP-1).

At the cellular and molecular levels, the impact of UV-B and UV-A radiation induces various reactions, including direct and indirect induction of DNA lesions.

Among the direct induction of DNA lesions, some are specific to UV radiation, for instance pyrimidine dimers and 6,4 photo-produced. In the event of an error during repair by the specialized enzymatic systems (nucleotide excision repair NER, or global excision repair GER), they may be responsible for mutations that are themselves the cause of tumoral processes resulting in the development of skin cancers. Moreover, in cells derived from these tumors, a very high incidence of mutations characteristic of solar UV impact is found. These DNA lesions are also the cause of apoptosis processes inducing the formation of characteristic cells in the epidermis, the "sunburn cells". It will also be noted that UV is responsible at the cellular level for the generation of reactive oxygen species, which are themselves the cause of many biological effects, such as the induction of oxidative DNA damage (8-oxoguanine) or the induction of numerous genes.

Finally, in addition to the effects mainly described on the two major cell types of the skin, namely the keratinocytes that form the stratified and differentiated epidermis, and the fibroblasts that are responsible for the synthesis and renewal of the dermal extracellular matrix, UV rays also have an impact on the Langerhans cells, which have an antigen-presenting immunity function.

The deleterious effects of UV rays on the skin (erythema, photocarcinogenesis, photoaging, photo-immunosuppression, etc.) are induced by the direct action of UV rays on certain cellular chromophores such as DNA, but also by indirect action. Specifically, the energy transported by UV rays is capable of triggering the formation of activated oxygen species (AOS), for instance singlet oxygen and the superoxide anion, by means of a photosensitization reaction involving endogenous photosensitizers such as riboflavins, bilirubins, phaeomelanin and porphyrin derivatives. The singlet oxygen and the superoxide anion undergo a cascade of reactions resulting in the production of other AOSs such as hydrogen peroxide and hydroxyl radicals. The AOSs thus generated damage DNA, cell membranes and certain proteins (enzymes, transcription factors, etc.).

Cells are equipped with an enzymatic antioxidant defense (Cu—Zn and Mn superoxide dismutases, catalases, glutathione peroxidases, etc.) and non-enzymatic antioxidant defense (vitamins E and C, thiols including glutathione, β-carotene, trace elements, etc.), whose role is to maintain the intracellular redox potential, but this defense capacity may be overloaded during an episode of intense oxidative stress.

The tripeptide glutathione (γ-L-glutamyl-L-cysteinylglycine or GSH) is the most widely occurring and abundant of the low molecular weight non-protein thiols. The majority of the intracellular GSH is found in reduced form (GSH). Glutathione disulfide (GSSG) is less than 0.5% of the total GSH. In most animal cells, the concentration of GSH is from 1 and 10 mM, whereas it is from about 0.5 and 10 μM in the plasma. The thiol function located on the cysteine residue gives it a redox potential (about −230 mV) that is predominant in redox metabolic phenomena. Its reductive and nucleophilic properties play a major role in protection against the oxidative impairment of fats, proteins and nucleic acids. Under a situation of oxidative stress, its protective and detoxifying role results mainly from its function as a coenzyme of glutathione peroxidases and glutathione-S-transferases. It also undergoes synergistic interactions with other components of the antioxidant protection system such as vitamin C, vitamin E, and superoxide dismutases.

Reducing the level of glutathione will thus affect the redox cellular balance. It is especially known that exposure to UV rays results in depletion of the level of intracellular GSH, thus increasing the sensitivity of the cells towards the oxidative stress.

Skin can be protected against the harmful effects of UV radiation by application of sunscreens. These products contain molecules that absorb the harmful wavelengths before they reach the skin and damage it, thus preventing the acute and chronic effects of exposure to UV rays.

However, sunscreens do not have a global action. Although no screening agent exists that allows total absorption of the harmful wavelengths (UV-B, UV-A and long UV-A), a photoprotection strategy based on induction of the endogenous antioxidant defense systems offers advantageous perspectives.

Thus, a real need exists to find or develop additional solutions in this field to reconstitute and/or preserve the level of endogenous glutathione after exposure to UV rays. This may be envisaged by stimulation with an active agent of the natural endogenous systems of cellular defense and/or repair after an episode of UV-induced stress.

Lipoic or thioctic acid (1,2-dithiacyclopentane-3-valeric acid) is an endogenous dithiol widely found in plants and animals. It is a coenzyme of fat and carbohydrate metabolism in mitochondrial multienzyme complexes such as pyruvate dehydrogenase and α-ketoglutarate dehydrogenase. Lipoic acid also increases the cellular level of glutathione by regenerating oxidized glutathione (GSSG) and increasing the activity of γ-glutamylcysteine ligase (an enzyme that controls the synthesis of GSH).

WO 2008/058 999 discloses siloxane or silane dithiolane compounds for increasing the level of glutathione after UV-induced depletion, especially the compound 5-(1,2-dithiolan-3-yl)-N-[3-(trimethylsilyl)propyl]pentanamide and the compound (trimethylsilyl)methyl 5-(1,2-dithiolan-3-yl) pentanoate. However, the protection afforded by these active agents against the UV-A daylight-induced depletion of GSH is still not fully satisfactory.

SUMMARY OF THE INVENTION

It has now been discovered that certain particular dithiolane compounds of formula (I) that will be defined in detail hereinbelow make it possible to significantly increase the level of glutathione after UV-induced depletion when compared with the dithiolane compounds of the prior art, and thus make it possible to reinforce and/or preserve the natural antioxidant protection of the skin against oxidative stress caused especially by UV radiation.

The present invention thus features the cosmetic formulation of at least one dithiolane compound of formula (I) into a composition comprising a physiologically acceptable medium, for the purpose of reinforcing and/or preserving the natural antioxidant protection of skin, notably the endogenous system of antioxidant defense against oxidative stress caused especially by UV radiation.

The present invention in particular features the cosmetic formulation of at least one dithiolane compound of formula (I) into a composition comprising a physiologically acceptable medium, for the purpose of reinforcing and/or preserving the level of endogenous intracellular glutathione that imparts to the skin natural antioxidant protection.

The term "skin" means any cutaneous surface of the human body, including skin, mucous membranes and semi-mucous membranes, thus including the lips, the scalp and also the skin integuments, especially the nails, bodily hair and head hair.

According to the invention, a "physiologically acceptable medium" is either a medium that is cosmetically or pharmaceutically acceptable with the skin, mucous membranes, the nails and/or the hair, or a medium that can be administered orally.

Other aspects of the invention will be defined hereinafter.

Figure 1:
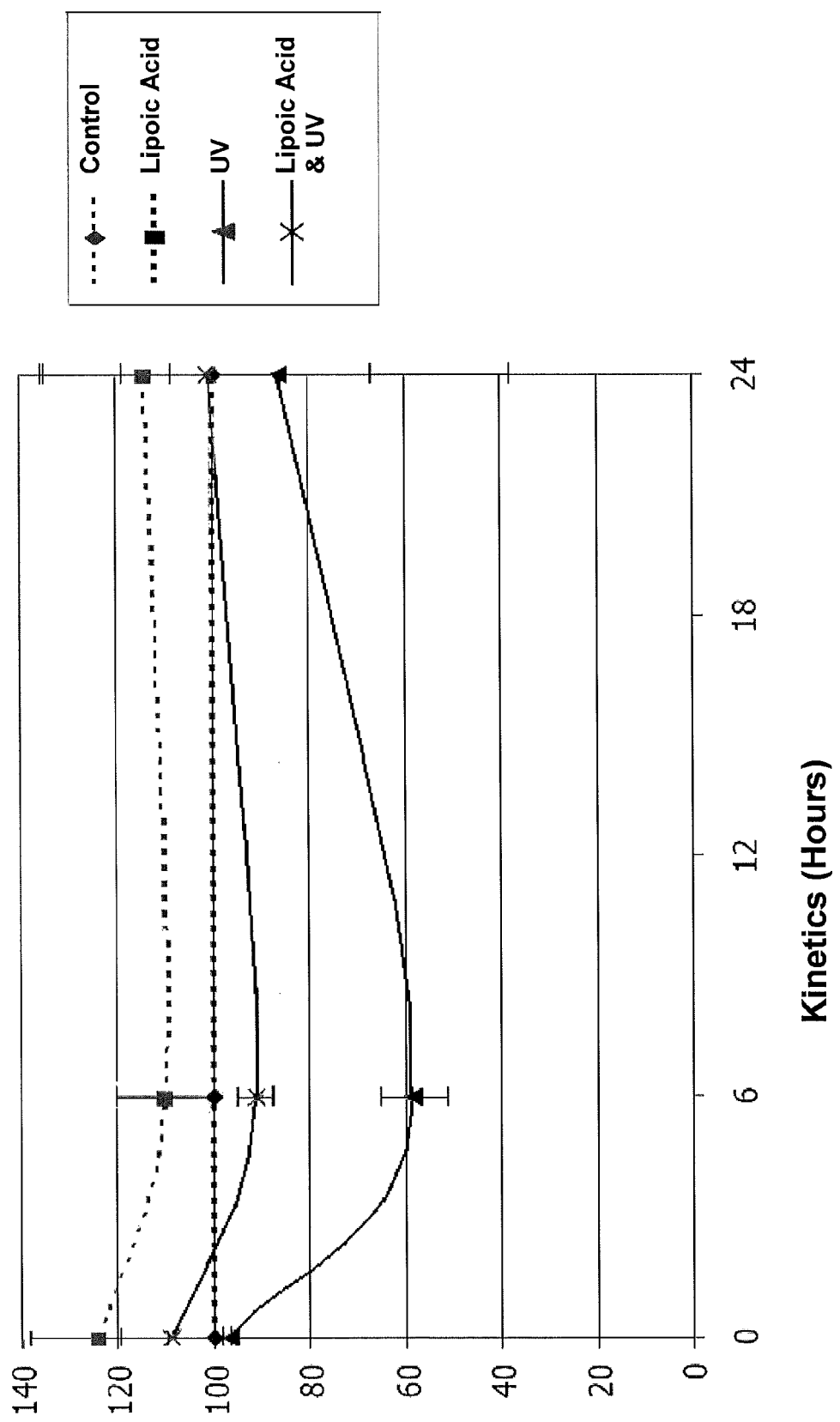
FIG. 1 is a graph showing the evaluation of the protective effect of lipoic acid in the MCB test on HaCaT.

DETAILED DESCRIPTION OF BEST MODE AND SPECIFIC/PREFERRED EMBODIMENTS OF THE INVENTION

The dithiolane compounds in accordance with the present invention correspond to formula (I) below:

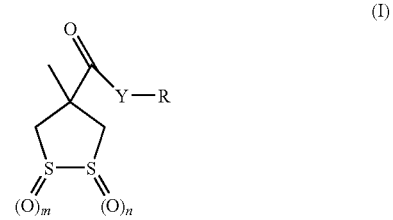

in which:
Y is O, $NR_1$ or S;
$R_1$ is a hydrogen atom, a saturated linear $C_1$-$C_{20}$ or branched $C_3$-$C_{20}$ or unsaturated $C_2$-$C_{20}$ alkyl hydrocarbon-based radical, a phenyl radical optionally substituted with one or more hydroxyl groups and/or with one or more $C_1$-$C_8$ alkoxy radicals;
R is a hydrogen atom, a saturated linear $C_1$-$C_{20}$ or branched $C_3$-$C_{20}$ or unsaturated $C_2$-$C_{20}$ alkyl hydrocarbon-based radical; a phenyl radical optionally substituted with one or more hydroxyl groups and/or with one or more $C_1$-$C_8$ alkoxy radicals, or a saturated $C_1$-$C_8$ alkyl radical containing a phenyl substituent optionally substituted with one or more hydroxyl groups and/or with one or more $C_1$-$C_8$ alkoxy radicals;
R optionally bears one or more substituents selected from among $OR_2$, $SR_2$, $NR_2R_3$ and $COOR_2$ in which:
$R_2$ is a hydrogen atom or a saturated linear $C_1$-$C_5$ or branched $C_3$-$C_5$ or unsaturated $C_2$-$C_5$ hydrocarbon-based radical, or a phenyl radical;
$R_3$ is a hydrogen atom, a saturated linear $C_1$-$C_5$ or branched $C_3$-$C_5$ or unsaturated $C_2$-$C_5$ hydrocarbon-based radical, a phenyl radical, or an acetyl radical, with the proviso that when Y is $NR_1$, R and $R_1$ may together form a ring member selected from among pyrrolidine, pyrroline, piperazine, morpholine, thiomorpholine and azepine;
m=0 or 1 or 2;
n=0 or 1 or 2;
and also the salts, chelates, solvates and optical isomers thereof.

The salts of the compounds described in the present invention include conventional non-toxic salts of the said compounds, such as those formed from organic or mineral acids. Exemplary thereof are the salts of mineral acids, such as sulfuric acid, hydrochloric acid, hydrobromic acid, hydriodic acid, phosphoric acid or boric acid. Also exemplary are the salts of organic acids, which may include one or more carboxylic, sulfonic or phosphonic acid groups. They may be linear, branched or cyclic aliphatic acids, or alternatively aromatic acids. These acids may also include one or more heteroatoms selected from O and N, for example in the form of hydroxyl groups. Exemplary are propionic acid, acetic acid, terephthalic acid, citric acid and tartaric acid and the salts of organic or mineral bases such as the triethanolamine, aminopropanediol, sodium or zinc salts.

The solvates that are acceptable for the non-therapeutic administration of the compounds described in the present invention include conventional solvates such as those formed during the final step of preparation of the said compounds due to the presence of solvents. Exemplary are the solvates due to the presence of water or of linear or branched alcohols such as ethanol or isopropanol.

The optical isomers are especially enantiomers and diastereoisomers.

Preferentially, the alkoxy radicals are linear $C_1$-$C_4$ radicals and more preferentially methoxy, ethoxy, propoxy or butoxy and even more preferentially methoxy.

Preferentially, the hydrocarbon-based radicals are linear or branched alkyls and may be selected from: methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl.

More preferentially, the hydrocarbon-based radicals are saturated linear or branched $C_1$-$C_8$ alkyl radicals: methyl, ethyl, propyl, isopropyl, butyl, isobutyl, tert-butyl, pentyl, hexyl, heptyl, octyl.

Preferably, the compounds of formula (I) include the following:

Y is S, O or $NR_1$;

$R_1$ is a hydrogen atom, a saturated linear $C_1$-$C_{10}$ or branched $C_3$-$C_{10}$ alkyl hydrocarbon-based radical;

R is a hydrogen atom, a saturated linear $C_1$-$C_{20}$ or branched $C_3$-$C_{20}$ alkyl hydrocarbon-based radical, a phenyl radical optionally substituted with one or more hydroxyl groups and/or with one or more $C_1$-$C_3$ alkoxy radicals, a saturated $C_1$-$C_5$ alkyl radical bearing a phenyl substituent optionally substituted with one or more hydroxyl groups and/or with one or more $C_1$-$C_3$ alkoxy radicals, a linear $C_1$-$C_5$ alkyl hydrocarbon-based radical substituted with one or more identical or different radicals selected from among $OR_2$, $SR_2$, $NR_2R_3$ and $COOR_2$ in which:

$R_2$ is a hydrogen atom or a saturated linear $C_1$-$C_5$ or branched $C_3$-$C_5$ or unsaturated $C_2$-$C_5$ hydrocarbon-based radical;

$R_3$ is a hydrogen atom, a saturated linear $C_1$-$C_5$ or branched $C_3$-$C_5$ hydrocarbon-based radical; a phenyl radical, an acetyl radical;

with the proviso that when Y=$NR_1$, R and $R_1$ may together form a pyrrolidine ring;

n=0 or 1 or 2;

m=0 or 1 or 2;

and also the acid or base salts, chelates, solvates and optical isomers thereof.

More preferentially, the compounds of formula (I) include the following:

Y is O or $NR_1$;

$R_1$ is a hydrogen atom, a saturated linear $C_1$-$C_{10}$ or branched $C_3$-$C_{10}$ alkyl hydrocarbon-based radical;

R is a hydrogen atom, a saturated linear $C_1$-$C_{10}$ or branched $C_3$-$C_{10}$ alkyl hydrocarbon-based radical, a phenyl radical optionally substituted with one or more hydroxyl groups and/or with one or more methoxy radicals, a saturated $C_1$-$C_3$ alkyl hydrocarbon-based radical bearing a phenyl substituent optionally substituted with one or more hydroxyl groups and/or with one or more methoxy radicals, a linear $C_1$-$C_4$ alkyl hydrocarbon-based radical substituted with one or more identical or different radicals selected from among $OR_2$, $SR_2$, $NR_2R_3$ and $COOR_2$ in which:

$R_2$ is a hydrogen atom or a saturated linear $C_1$-$C_5$ or branched $C_3$-$C_5$ hydrocarbon-based radical;

$R_3$ is a hydrogen atom, a saturated linear $C_1$-$C_5$ or branched $C_3$-$C_5$ hydrocarbon-based radical;

n=0 or 1 or 2;

m=0 or 1 or 2;

and also the acid or base salts, chelates, solvates and optical isomers thereof.

Even more preferentially, the compounds of formula (I) include the following:

Y is $NR_1$;

$R_1$ is a hydrogen atom, a saturated linear $C_1$-$C_4$ alkyl hydrocarbon-based radical;

R is a hydrogen atom, a saturated linear $C_1$-$C_{10}$ or branched $C_3$-$C_{10}$ alkyl hydrocarbon-based radical, a phenyl radical, a saturated linear $C_1$-$C_4$ alkyl radical substituted with a phenyl radical optionally substituted with one or more identical or different groups selected from OH and OMe, a linear $C_1$-$C_4$ alkyl hydrocarbon-based radical substituted with one or more identical or different radicals selected from among OH, NHAc, $SR_2$ and $COOR_2$ wherein $R_2$ is a hydrogen atom or a linear $C_1$-$C_4$ alkyl radical;

n=0 or 1 or 2, m=0 or 1 or 2;

and also the acid or base salts, chelates, solvates and optical isomers thereof.

Even more particularly, the compounds of formula (I) include the following:

Y is NH;

R is a hydrogen atom, a saturated linear $C_1$-$C_{10}$ or branched $C_3$-$C_{10}$ alkyl hydrocarbon-based radical, a phenyl radical, a saturated linear $C_1$-$C_4$ alkyl radical substituted with a phenyl radical optionally substituted with one or more identical or different groups selected from OH and OMe, a linear $C_1$-$C_4$ alkyl hydrocarbon-based radical substituted with one or more identical or different radicals selected from among OH, NHAc, $SR_2$ and $COOR_2$ wherein $R_2$ is a hydrogen atom or a linear $C_1$-$C_4$ alkyl radical;

n=0 or 1 or 2;

m=0 or 1 or 2;

and also the acid or base salts, chelates, solvates and optical isomers thereof.

Still even more particularly, the compounds of formula (I) include the following:

Y is NH;

R is a hydrogen atom, a saturated linear $C_1$-$C_{10}$ or branched $C_3$-$C_{10}$ alkyl hydrocarbon-based radical;

n=0 or 1 or 2;

m=0 or 1 or 2;

and also the acid or base salts, chelates, solvates and optical isomers thereof.

Preferentially, Y=O or $NR_1$.

More preferentially, Y=$NR_1$.

Even more preferentially, Y=NH.

Most preferentially, R=H or a $C_1$-$C_8$ alkyl radical.

Among the compounds of formula (I) that will preferably be administered are the following:

| No. | Structure | Chemical name |
|---|---|---|
| 1. | ![structure with CO2H and S-S dithiolane ring] | 4-methyl-1,2-dithiolane-4-carboxylic acid |

| No. | Structure | Chemical name |
|-----|-----------|---------------|
| 2. | 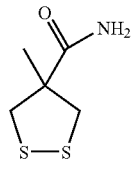 | 4-methyl-1,2-dithiolane-4-carboxamide |
| 3. | 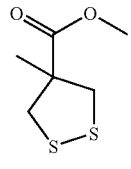 | methyl 4-methyl-1,2-dithiolane-4-carboxylate |
| 4. | 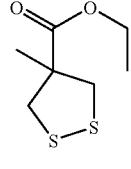 | ethyl 4-methyl-1,2-dithiolane-4-carboxylate |
| 5. | 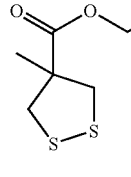 | propyl 4-methyl-1,2-dithiolane-4-carboxylate |
| 6. | 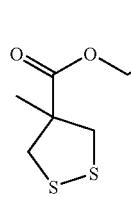 | benzyl 4-methyl-1,2-dithiolane-4-carboxylate |
| 7. | 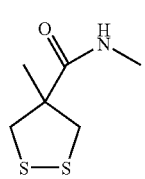 | N-methyl-4-methyl-1,2-dithiolane-4-carboxamide |
| 8. | 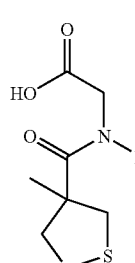 | {[(4-methyl-1,2-dithiolan-4-yl)carbonyl]amino}acetic acid |
| 9. | 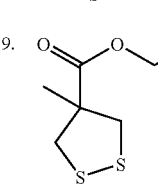 | octyl 4-methyl-1,2-dithiolane-4-carboxylate |

-continued

| No. | Structure | Chemical name |
|---|---|---|
| 10. | 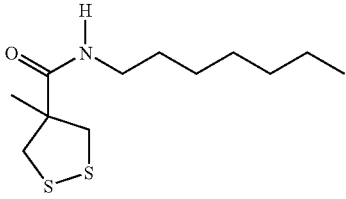 [SMILES: CCCCCCCNC(=O)C1(C)CSSC1] | N-heptyl-4-methyl-1,2-dithiolane-4-carboxamide |
| 11. | 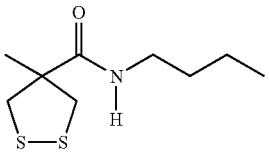 | N-butyl-4-methyl-1,2-dithiolane-4-carboxamide |
| 12. | 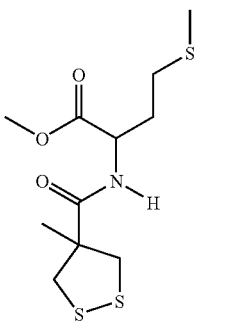 | methyl 2-{[(4-methyl-1,2-dithiolan-4-yl)carbonyl]amino}-4-(methylsulfanyl)butanoate |
| 13. | 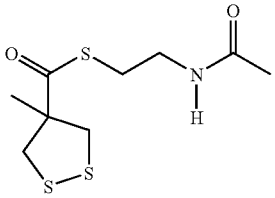 | S-[2-(acetylamino)ethyl]4-methyl-1,2-dithiolane-4-carbothioate |
| 14. | 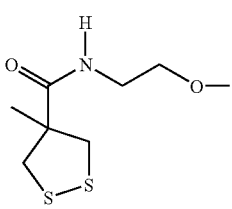 | N-(2-hydroxyethyl)-4-methyl-1,2-dithiolane-4-carboxamide |
| 15. | 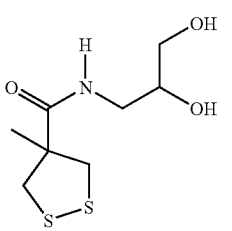 | N-(2,3-dihydroxypropyl)-4-methyl-1,2-dithiolane-4-carboxamide |
| 16. | 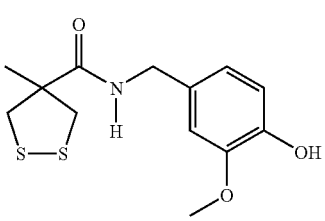 [SMILES: COc1cc(CNC(=O)C2(C)CSSC2)ccc1O] | N-(4-hydroxy-3-methoxybenzyl)-4-methyl-1,2-dithiolane-4-carboxamide |

| No. | Structure | Chemical name |
|---|---|---|
| 17. | 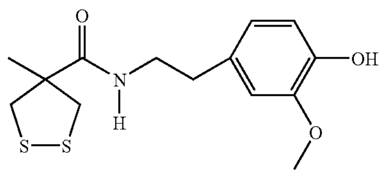 [SMILES: COc1cc(CCNC(=O)C2(C)CSSC2)ccc1O] | N-[2-(4-hydroxy-3-methoxyphenyl)ethyl]-4-methyl-1,2-dithiolane-4-carboxamide |
| 18. | 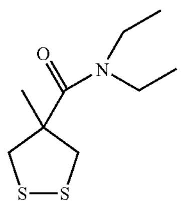 | N,N-diethyl-4-methyl-1,2-dithiolane-4-carboxamide |
| 19. | 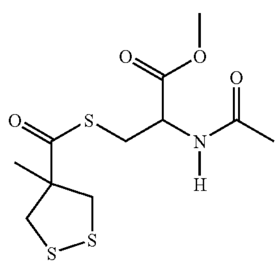 [SMILES: COC(=O)C(CSC(=O)C1(C)CSSC1)NC(C)=O] | methyl 2-(acetylamino)-3-{[(4-methyl-1,2-dithiolan-4-yl)carbonyl]sulfanyl}propanoate |
| 20. | 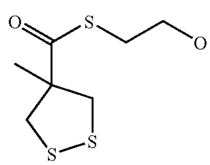 | S-(2-hydroxyethyl) 4-methyl-1,2-dithiolane-4-carbothioate |
| 21. | 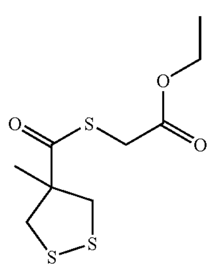 | ethyl {[(4-methyl-1,2-dithiolan-4-yl)carbonyl]sulfanyl}acetate |
| 22. | 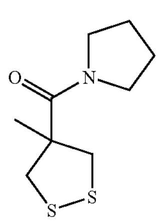 | [(4-methyl-1,2-dithiolan-4-yl)carbonyl]pyrrolidine |
| 23. | 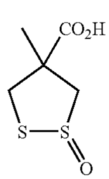 | 4-methyl-1,2-dithiolane-4-carboxylic acid 1-oxide |

-continued

| No. | Structure | Chemical name |
|---|---|---|
| 24. | 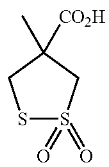 | 4-methyl-1,2-dithiolane-4-carboxylic acid 1,1-dioxide |
| 25. | 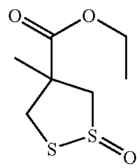 | ethyl 4-methyl-1,2-dithiolane-4-carboxylate 1-oxide |
| 26. | 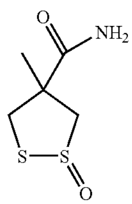 | 4-methyl-1,2-dithiolane-4-carboxamide 1-oxide |
| 27. | 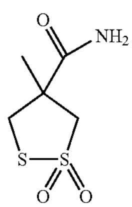 | 4-methyl-1,2-dithiolane-4-carboxamide 1,1-dioxide |
| 28. | 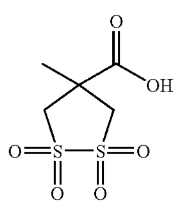 | 4-methyl-1,2-dithiolane-4-carboxylic acid 1,1,2,2-tetroxide |
| 29. | 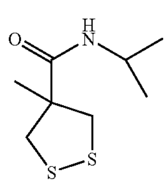 | 4-methyl-N-(1-methylethyl)-1,2-dithiolane-4-carboxamide |
| 30. | 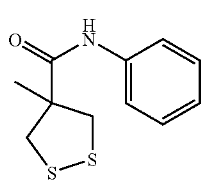 | 4-methyl-N-phenyl-1,2-dithiolane-4-carboxamide |
| 31. | 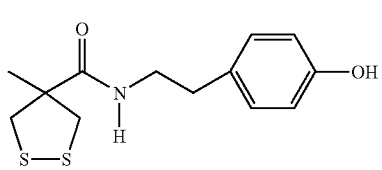 [SMILES: CC1(C(=O)NCCc2ccc(O)cc2)CSSC1] | N-[2-(4-hydroxyphenyl)ethyl]-4-methyl-1,2-dithiolane-4-carboxamide |

-continued

| No. | Structure | Chemical name |
|---|---|---|
| 32. | 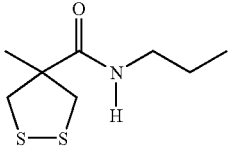 | N-propyl-4-methyl-1,2-dithiolane-4-carboxamide |
| 33. | 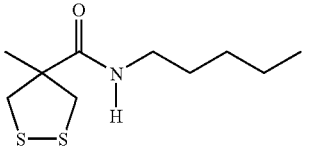 | N-pentyl-4-methyl-1,2-dithiolane-4-carboxamide |
| 34. | 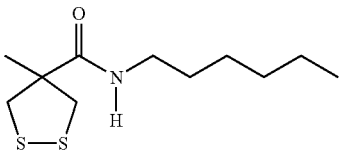 | N-hexyl-4-methyl-1,2-dithiolane-4-carboxamide |
| 35. | 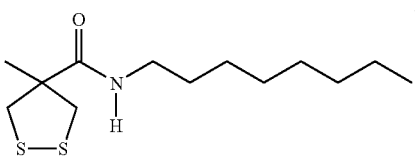 [SMILES: CCCCCCCCNC(=O)C1(C)CSSC1] | N-octyl-4-methyl-1,2-dithiolane-4-carboxamide |
| 36. | 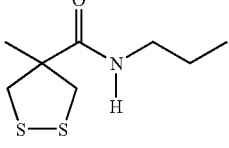 | N-propyl-4-methyl-1,2-dithiolane-4-carboxamide |
| 37. | 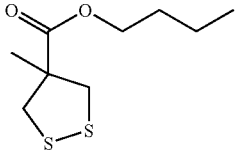 | butyl 4-methyl-1,2-dithiolane-4-carboxylate |
| 38. | 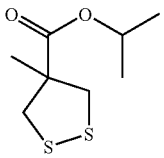 | isopropyl 4-methyl-1,2-dithiolane-4-carboxylate |
| 39. | 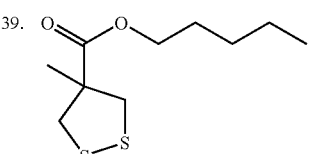 | pentyl 4-methyl-1,2-dithiolane-4-carboxylate |
| 40. | 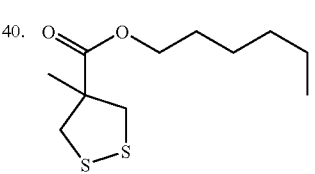 | hexyl 4-methyl-1,2-dithiolane-4-carboxylate |

-continued

| No. | Structure | Chemical name |
|---|---|---|
| 41. | 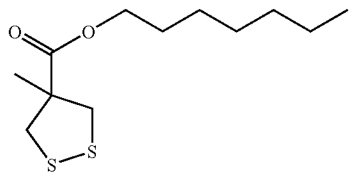 [SMILES: CCCCCCCOC(=O)C1(C)CSSC1] | heptyl 4-methyl-1,2-dithiolane-4-carboxylate |

Among these compounds, the following compounds are more particularly preferred:

| No. | Structure | Chemical name |
|---|---|---|
| 1. | 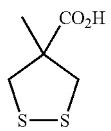 | 4-methyl-1,2-dithiolane-4-carboxylic acid |
| 2. | 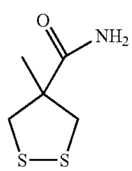 | 4-methyl-1,2-dithiolane-4-carboxamide |
| 9. | 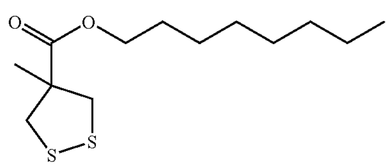 [SMILES: CCCCCCCCOC(=O)C1(C)CSSC1] | octyl 4-methyl-1,2-dithiolane-4-carboxylate |
| 10. | 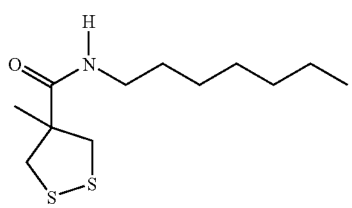 [SMILES: CCCCCCCNC(=O)C1(C)CSSC1] | N-heptyl-4-methyl-1,2-dithiolane-4-carboxamide |
| 26. | 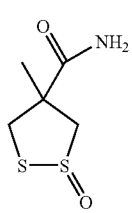 | 4-methyl-1,2-dithiolane-4-carboxamide 1-oxide |
| 27. | 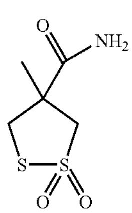 | 4-methyl-1,2-dithiolane-4-carboxamide 1,1-dioxide |

Certain of the compounds in accordance with the invention are known per se. These are the compounds 1 to 8 below:

| No. | Structure | Chemical name | CAS |
|---|---|---|---|
| 1. | 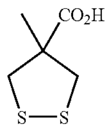 | 4-methyl-1,2-dithiolane-4-carboxylic acid | 208243-72-5 |
| 2. | 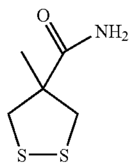 | 4-methyl-1,2-dithiolane-4-carboxamide | 208243-73-6 |
| 3. | 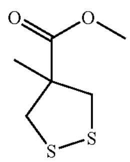 | methyl 4-methyl-1,2-dithiolane-4-carboxylate | 208243-88-3 |
| 4. | 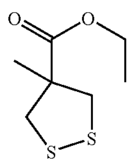 | ethyl 4-methyl-1,2-dithiolane-4-carboxylate | 208243-89-4 |
| 5. | 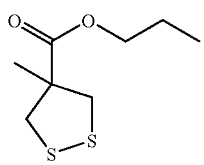 | propyl 4-methyl-1,2-dithiolane-4-carboxylate | 208243-90-7 |
| 6. | 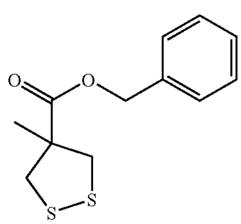 [SMILES: CC1(C(=O)OCc2ccccc2)CSSC1] | benzyl 4-methyl-1,2-dithiolane-4-carboxylate | 208243-73-6 |
| 7. | 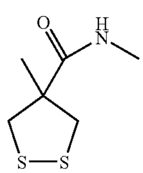 | N-methyl-4-methyl-1,2-dithiolane-4-carboxamide | 208243-91-8 |
| 8. | 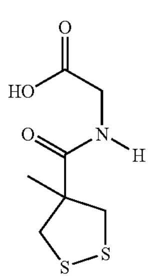 | {[(4-methyl-1,2-dithiolan-4-yl)carbonyl]amino}acetic acid | 208243-74-7 |

These compounds have been described in WO 98/23606 for use in pharmacology as agents for reducing blood fat or glucose.

The compounds of formula (I) with the exception of the compounds 1 to 8 are novel and constitute another aspect of the invention.

This invention also features cosmetic or pharmaceutical compositions comprising, formulated into a physiologically acceptable medium, at least one compound of formula (I) with the exception of the compounds 1 to 8 as defined above.

Synthesis:

The compounds of formula (I) may be prepared according to the routes described below and documented in the review by Lene Teuber, Sulfur reports, 9(4), 257-349, 1990, Naturally occurring 1,2-dithiolanes and 1,2,3-trithianes. Chemical and Biological Properties. EP-0-869,126 A1.

Starting with 2,2-bis(hydroxymethyl)propionic acid (CAS: 4767-03-7), by functionalization of the hydroxyls as leaving groups X (alkyl or aryl sulfonates such as mesylates or tosylates or halogens such as iodine, bromine or chlorine) followed by the introduction of sulfur according to the following reaction scheme:

Organic Transformations by R. Larock, Wiley VCH Ed. in the chapter: Interconversion of the nitriles, carboxylic acids and derivatives). Preferably, the methods used favor proceeding via the acid chloride (by using thionyl or oxalyl chloride, or 1-chloro-N,N,2-trimethyl-1-propenamine) or via the formation of a mixed anhydride (using alkyl chloroformates) or the use of carbodiimides or diethyl cyanophosphate (Phosphorus in organic synthesis—XI, Amino acids and peptides—XXI, Reaction of diethyl phosphorocyanidate with carboxylic acids. A new synthesis of carboxylic esters and amides, Tetrahedron, 32, 1976, 2211-2217).*

The solvents used may be polar or apolar, and protic or aprotic (for example toluene, dichloromethane, THF, DMF, acetonitrile, water, methanol or isopropanol).

All these reactions may be carried out at temperatures of from −20 to 100° C.

The production of the products of oxidation of the sulfur atoms of the dithiolanes of formula (I) (m and n other than zero) may be performed according to the following reaction scheme:

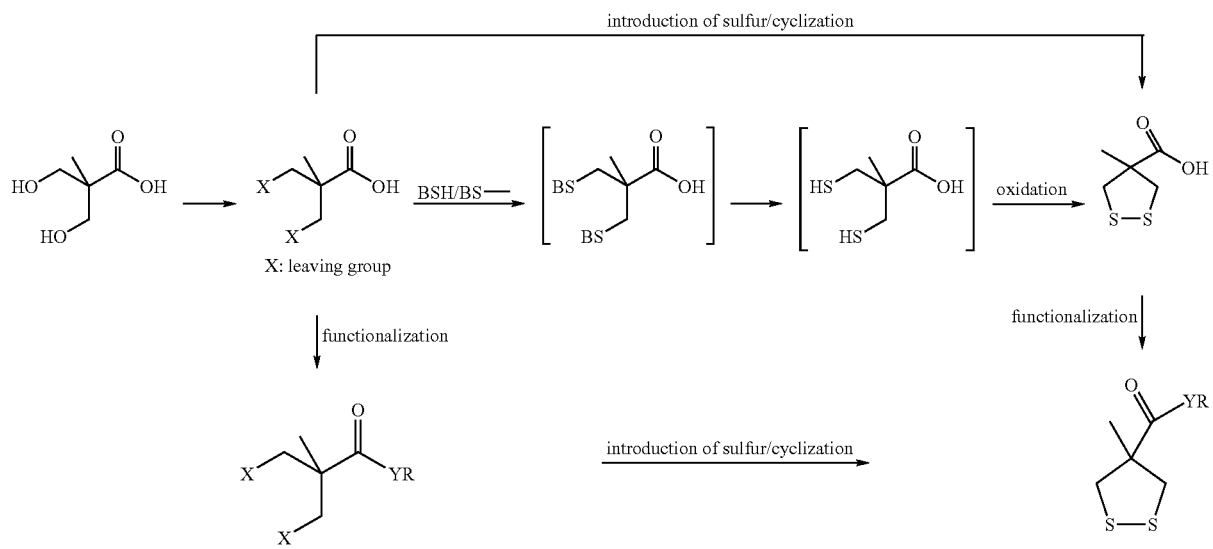

This introduction of sulfur may be performed:

(i) in one step using a metal disulfide (such as $Na_2S_2$) or tetrathiomolybdate salts in polar protic or aprotic solvents (for example water, DMF, methanol or acetonitrile) to give the dithiolane;

(ii) or in two steps by forming a dithiol intermediate, which, in the presence of an oxidizing agent (oxygen, DMSO, $FeCl_3$, $I_2$, $Br_2$, sodium iodide, thallium trifluoroacetates, silver triflates, hydrogen peroxide, sodium iodate, sodium periodate, sodium hypochlorite, potassium ferricyanide or chromium oxide), in neutral or basic medium, leads to the formation of the dithiolane. In this case, the dithiol is obtained by transformation (in basic or acidic medium) in a polar or apolar solvent of an intermediate species via thioacetic acid derivatives $CH_3COSH$ (in the presence of base), with thiourea or NaSH, via the formation of dithiosulfonates (Bunte salts).

Functionalization of the carboxylic acid COOH into a function COYR may be performed according to the conventional acid activation methods (described in Comprehensive using oxidizing agents such as oxygen, hydrogen peroxide, DMSO, sodium periodate, organic peracids, inorganic persulfates or inorganic permanganates in the presence or absence of a catalyst (for example $Na_2WO_4$, $MoO_2Cl_2$ or trichlorooxobis(triphenylphosphine)rhenium). The various oxidation steps depend on the stoichiometry of the oxidizing agents used. The solvents that may be used may be water, acetone, dichloromethane or methanol.

These oxidations have been described in the following publications:

Oxidation of 1,2-Dithiolanes, Bernt Lindberg, Göran Bergson, Arkiv För Kemi, 1965, 23(31), 319-333;

Selective oxidation of sulfides to sulfoxides and sulfones at room temperature using $H_2O_2$ and an Mo(VI) salt as catalyst, Kandasamy Jeyakumar, Dillip Kumar Chand, Tetrahedron Letters 47 (2006), 4573-4576;

Rhenium-Catalyzed Oxidation of Thiols and Disulfides with Sulfoxides, Jeffrey B. Arterburn, Marc C. Perry, Sherry L. Nelson, Benjamin R. Dible, Mylena S. Holguin, J. Am. Soc., 119, 9309-9310, 1997.

Advantageously, compound 1 may be obtained according to the route described below starting with dichloropivalic acid according to a one-pot process, ending with a precipitation.

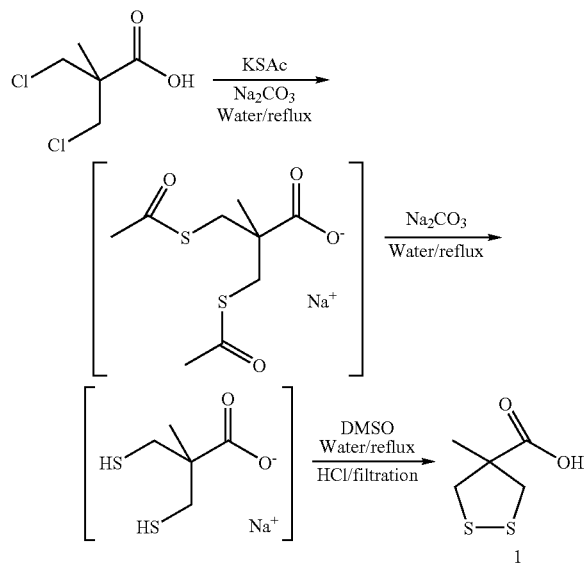

Advantageously, compound 2 may be obtained from compound 1, preferentially using isobutyl chloroformate or oxalyl chloride.

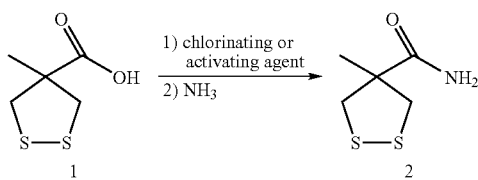

The assignee hereof has demonstrated that UV daylight (simulation of average UV daylight, L'Oréal concept, Christiaens F. J. et al.: Standard ultraviolet daylight for non-extreme exposure conditions, Photochem. Photobiol., 2005) leads to a decrease in the level of intracellular GSH on HaCaT cells (keratinocytes obtained from an adult human skin implant spontaneously immortalized in vitro). The depletion is maximal 6 hours after exposure (about 40% decrease) and return to the basal level occurs 24 hours after exposure to the UV daylight (UV-DL).

The compounds according to the invention can prevent and/or correct this depletion of GSH, and can thus "boost" the endogenous antioxidant defense systems, so as to prepare the skin to better withstand UV stress and to help it to repair itself.

Their activity was compared with a reference compound, lipoic acid, which is known to increase the level of GSH.

It has thus now been shown that the capacity of the compounds according to the invention for increasing the level of GSH was much greater than that of lipoic acid, measured under the same conditions (see Example 17).

The present invention in particular features the cosmetic use of at least one dithiolane compound selected from those of formula (I) in a composition comprising a physiologically acceptable medium, for the purpose of reinforcing and/or preserving the level of endogenous intracellular glutathione that gives the skin natural antioxidant protection against oxidative stress caused especially by UV radiation.

Thus, administration according to the invention can reinforce and/or preserve the cellular antioxidant defense systems, in particular the antioxidant defense systems of skin cells. The skin cells are especially fibroblasts, keratinocytes and Langerhans cells.

According to one advantageous embodiment of the invention, the compounds of general formula (I) are useful as skin photoprotective agents.

This use is whether the skin has undergone exposure to daylight of an intensity lower than the minimum erythemal dose and whose effects do not produce visible signs on the skin, or whether the UV-ray damage is visible, for example by the appearance of redness on the skin.

Consequently, the impairments range from simple discomfort such as a uniquely perceptible sensation of heating of the skin, to redness, or even irritation.

Thus, the compounds of general formula (I) are useful for preventing and/or treating UV stress and/or heating sensations caused by solar radiation, in particular UV-A and/or UV-B.

The compounds of general formula (I) are also useful for preparing a composition, comprising a physiologically acceptable medium, for preventing and/or treating skin impairments, such as skin redness and irritation, caused by solar radiation.

The compounds of general formula (I) are also useful for the preparation of a composition, comprising a physiologically acceptable medium, for preventing and/or treating DNA lesions caused by solar radiation and thus for preventing the development of cancers, in particular skin cancers.

The compounds of general formula (I) are also useful for the preparation of a composition containing a physiologically acceptable medium, which is useful for treating skin and/or mucous membrane disorders induced by irradiation with UV-A and/or UV-B radiation.

Solar irradiation or exposure is characterized by an exposure to sunlight, and may especially be an intense irradiation corresponding to exposure to zenithal sunlight or to solar radiation varying by an angle of 30° around this zenithal position and/or when the skin is subjected to UV radiation capable of inducing a solar erythema (redness commonly known as "sunburn"), and defined by a minimum erythemal dose (MED). This dose varies as a function of the phototype of the individual and of the UV-A/UV-B ratio.

The present invention especially features a regime or regimen for preventing or reducing damage induced in the skin, mucous membranes and/or the integuments of a mammal, in particular of a human being, by short exposure to erythemal doses of solar radiation.

These solar exposure conditions comprise UV-A and/or UV-B rays, at doses around the MED, in particular at a dose of greater than or equal to 1 MED.

As explained above, by virtue of their capacity for increasing the level of GSH, the compounds of formula (I) according to the invention allow the establishment of the cutaneous antioxidant protective system.

Thus, administration according to the invention of at least one dithiolane compound selected from those of formula (I) in a composition containing a physiologically acceptable medium is particularly suitable for preparing the skin for exposure to sunlight.

In particular, preparation of the skin for exposure to sunlight may be carried out by the daily application to the skin of the said cosmetic composition for one week, and preferably two weeks, before the exposure to sunlight, just up to at least one day (from 6 and 18 hours) before the exposure to sunlight.

Whether they are of endogenous or exogenous origin, free radicals cause substantial oxidative damage, especially in cell membranes (lipid peroxidation causing degradation of the membrane permeability), cell nuclei (destruction of DNA) and tissues, in particular connective tissue (degradation of elastin and collagen fibers, and depolymerization of polyuronic fibers). This damage especially leads to drying-out and loss of firmness and elasticity of the skin (Grinwald et al. 1980, Agren et al. 1997).

Specialists currently consider that one of the causes of cellular aging is the weakening of the defense capacities against free radicals and against the oxidation phenomena (especially the formation of superoxide ions) that they initiate.

Thus, more generally, the compounds of general formula (I) according to the invention are useful as indirect antioxidant compounds for preventing and/or limiting the formation of free radicals and/or for removing the free radicals present in cells, and may be used for any skin disorder caused by oxidative stress.

This activity of the compounds of general formula (I) is reinforced by the intrinsic antioxidant property of these compounds associated with their thiol function.

Thus, administration of the compounds according to the invention allows certain clinical signs of aging of the skin to be prevented and/or treated.

Aging is a natural physiological phenomenon whose clinical signs may generally be reflected on the skin by the appearance of wrinkles and fine lines, by slackening of the cutaneous and subcutaneous tissues, by a loss of skin elasticity and by atony of the texture of the skin. The loss of firmness and tonicity of the skin, for instance wrinkles and fine lines, is at least partly accounted for by dermal atrophy and also flattening of the dermo-epidermal junction; the skin is less firm and more flaccid, and the thickness of the epidermis decreases.

Another clinical sign of aging is the dry and coarse appearance of the skin, which is due essentially to greater desquamation; by diffracting light rays, these squamae also contribute towards the somewhat greyish appearance of the complexion.

Certain of these signs are more particularly associated with intrinsic or physiological aging, i.e., age-related aging, whereas others are more specific to extrinsic aging, i.e., aging caused in general by the environment; this is more particularly a case of photo-aging due to exposure to sunlight, light or any other radiation, or alternatively pollutants.

Thus, this invention is particularly suited for the cosmetic use of at least one compound of general formula (I) in a composition containing a physiologically acceptable medium, for preventing and/or treating loss of firmness and/or elasticity of the skin. Such a use especially allows the skin to regain a uniformly smooth appearance.

The present invention is also suited for the cosmetic use of at least one compound of general formula (I) according to the invention in a composition containing a physiologically acceptable medium, for preventing and/or treating skin dehydration.

This invention is also more generally suited for the cosmetic use of at least one compound selected from those of general formula (I) in a composition containing a physiologically acceptable medium, for preventing and/or treating epidermal atrophy and/or skin roughness and/or skin dryness.

The present invention also features the cosmetic use of at least one compound of general formula (I) in a composition containing a cosmetically acceptable medium, for preventing and/or treating the harmful effects of pollution on the skin.

It is known that the toxicity of atmospheric pollutants, especially gaseous pollutants such as sulfur dioxide, ozone and nitrogen oxides on the constituents of the skin (fibers, cells and enzymes) and on the sebum secreted by the skin is especially associated with their activity of free-radical initiators, which are a source of oxidation phenomena that cause cell damage in living beings.

The live cells, which are in direct and permanent contact with the external environment (especially the skin, the scalp and certain mucous membranes), are particularly sensitive to these effects of gaseous pollutants, which are especially reflected by accelerated aging of the skin, with early formation of wrinkles or fine lines, and also by a decrease in the vigor and dull appearance of the hair.

As explained previously, an adverse effect of the presence of free radicals in the skin is that they cause peroxidation of lipids. With age (more particularly from the age of forty), the accumulation of these peroxidized lipids is responsible for unpleasant body odor such as a rancid odor (Haze S. et al., *J. Invest. Dermatol.*, 2001, 116(4):520-4).

This invention features the cosmetic use of at least one compound of general formula (I) according to the invention in a composition containing a physiologically acceptable medium, for preventing and/or limiting and/or eliminating the peroxidation of skin lipids.

Thus, this invention is also useful for preventing and/or limiting and/or eliminating unpleasant body odor.

The compositions according to the invention may be useful for cosmetic and/or dermatological applications. They may be compositions suitable for topical application, in particular external topical application to the skin, mucous membranes and/or the integuments.

According to another embodiment, the compositions according to the invention are suitable for the oral route, and are especially useful for oral cosmetic applications.

The amount of compound that may be administered according to the invention obviously depends on the desired effect, and may thus vary within a wide range.

To provide an order of magnitude, the compound(s) of formula (I) as defined previously may be administered by the topical route, in particular the external topical route, in an amount representing from 0.001% to 20% of the total weight of the composition and preferentially in an amount representing from 0.01% to 10% of the total weight of the composition.

For the oral route, the compound(s) of formula (I) may be used in an amount of from 0.1 to 100 mg per dosage intake.

Formulation of the Compositions:

Preferably, the compositions according to the invention comprising at least one compound of formula (I) are constituted of a cosmetically acceptable medium, i.e., a medium that has a pleasant color, odor and feel and that does not cause any unacceptable discomfort.

The compositions are preferably cosmetic compositions or products. The term "cosmetic product" especially means any substance or preparation intended to be placed in contact with the various surface parts of the human body (epidermis, pilous and hair system, nails, lips and external genital organs) or with the teeth and the oral mucosae for the purpose, exclusively or mainly, for cleaning them, fragrancing them, modifying their appearance and/or correcting body odor and/or protecting them or keeping them in good condition (Amended Cosmetic Directive 76/768/EEC).

The compositions according to the invention may especially be in the form of an alcoholic, aqueous-alcoholic or oily solution, a suspension, a dispersion, a W/O, O/W or multiple emulsion, aqueous or anhydrous gels, or a vesicular dispersion of ionic or nonionic type. It may have a liquid, semi-liquid, pasty or solid consistency.

For topical application, the compositions according to the invention may especially be in the form of an aqueous-alcoholic or oily solution or a dispersion of the lotion or serum type, emulsions of liquid or semi-liquid consistency of the milk type, obtained by dispersing a fatty phase in an aqueous phase (O/W) or conversely (W/O) or multiple emulsions, a free or compacted powder to be used in unmodified form or to be incorporated into a physiologically acceptable medium, or suspensions or emulsions of soft consistency of the aqueous or anhydrous cream or gel type, or alternatively microcapsules or microparticles, or vesicular dispersions of ionic and/or nonionic type. They may thus be in the form of an ointment, a tincture, a cream, a pomade, a powder, a patch, an impregnated pad, a solution, an emulsion or vesicular dispersion, a lotion, a gel, a spray, a suspension, a shampoo, an aerosol or a mousse. They may be anhydrous or aqueous. They may also consist of solid preparations constituting soaps or cleansing bars.

These compositions are formulated according to the usual methods.

According to another embodiment of the invention, the compositions are suitable for oral administration, in particular "cosmetic oral" use.

For oral use, the compositions may especially be in the form of wafer capsules, gel capsules, Coated tablets, granules, plain tablets, chewable pastes, gels or drinkable syrups or in any other form known to those skilled in the art.

The amounts of the various constituents of the compositions that may be used according to the invention are those conventionally used in the fields under consideration.

Combinations:

The compositions according to the invention may also contain agents for reinforcing or complementing the activity of the compound of formula (I), and especially at least one compound selected from antioxidants, anti-pollution agents, organic screening agents and/or mineral screening agents, and agents for stimulating DNA repair.

The compounds of formula (I) according to the invention may also be advantageously combined with extracts (total biomass, culture medium, ribosomal fraction, cell membrane fraction, LPS fraction, lipid A, etc.) of non-fruiting, non-photosynthetic filamentous bacteria such as *Vitreoscilla filiformis* or alternatively {2-(acetyl(3-trifluoromethylphenyl)amino]-3-methylbutyrylamino}acetic acid.

It is thus possible, for example, to include an antioxidant selected from:

vitamin E (tocopherol) and derivatives thereof, including the acetate, linoleate or nicotinate, preferably at concentrations of about from 0.1% to 5%, γ-orizanol (0.1% to 5%), lysine pidolate or arginine pidolate (0.5% to 10%), plant extracts such as extract of balm (0.01% to 2%), extract of silymarin (0.01% to 2%), extract of *Ginkgo biloba* (0.05% to 2%), extract of sage (0.05% to 2%), extract of cola nuts (0.05% to 2%), extract of rutin (0.1% to 2%) or extract of thyme (0.1% to 2%), the percentages being given as dry matter, carotenoids, such as α- and β-carotene or lycopene in a purified form or in an extract (for example tomato puree with a lycopene titre reaching a final lycopene concentration of from $10^{-12}$% to 10% to more preferentially from $10^{-7}$% to 0.1%), proanthocyanidol oligomers from pine, hawthorn or grape (0.1% to 2%), di-tert-butylhydroxybenzylidenecamphor (0.1% to 2%), green tea (0.1% to 2%), caffeine (0.1% to 5%), glycerol (2% to 30%), mannitol (2% to 30%), carnosine (0.1% to 2%), superoxide dismutase (100 to 10 000 IU/100 g), guanosine (0.01% to 1%), microalgae containing ethoxyquine such as *Hematococcus* (0.005% to 1%), pentasodium aminotrimethylenephosphonate (0.001% to 0.5%), lactoperoxidase (0.01% to 0.1%), vitamin C and derivatives thereof, lactoferrin (0.01% to 0.1%), isopropyl (benzyl{2-[benzyl(2-isopropoxy-2-oxoethyl)amino]ethyl}amino)acetate, phloretin, hesperidin, neohesperidin dihydrochalcone, ferulic acid, Eukarions (including EUK-8, EUK-134 and EUK-189 developed by Proteome Systems), L-2-oxo-4-thiazolidinecarboxylic acid ergothioneine, caffeic acid, Desferal, 4,4'-(2,3-dimethylbutane-1,4-diyl)dibenzene-1,2-diol.

A mixture of several antioxidants may also be included.

Also exemplary are free-radical scavengers, in particular bioflavonoids; coenzyme Q10 or ubiquinone; certain enzymes such as catalase, glutathione peroxidase and quinone reductases; glutathione; benzylidenecamphor; benzylcyclanones; substituted naphthalenones; pidolates; phytanetriol; lignans; melatonin; hydroxylated chalcones, and also reduced derivatives thereof.

Preferably, the antioxidant is selected from vitamin C, vitamin E, isopropyl (benzyl{2-[benzyl(2-isopropoxy-2-oxoethyl)amino]ethyl}amino)acetate, ferulic acid, phloretin, neohesperidin dihydrochalcone and SOD.

The term "anti-pollution agent" means any compound capable of trapping ozone, monocyclic or polycyclic aromatic compounds such as benzpyrene and/or heavy metals such as cobalt, mercury, cadmium and/or nickel. The term "free-radical scavenger" means any compound capable of trapping free radicals.

As ozone-trapping agents that may be used in the compositions according to the invention, exemplary are in particular vitamin C and its derivatives including ascorbyl glucoside; phenols and polyphenols, in particular tannins, ellagic acid and tannic acid; epigallocatechin and natural extracts containing it; extracts of olive tree leaf; extracts of tea, in particular of green tea; anthocyans; extracts of rosemary; phenol acids, in particular chorogenic acid; stilbenes, in particular resveratrol; sulfur-containing amino acid derivatives, in particular S-carboxymethylcysteine; ergothioneine; N-acetylcysteine; chelating agents, for instance N,N'-bis(3,4,5-trimethoxybenzyl)ethylenediamine or one of its salts, metal complexes or esters; carotenoids such as crocetin; and various starting materials, for instance the mixture of arginine, histidine ribonucleate, mannitol, adenosine triphosphate, pyridoxine, phenylalanine, tyrosine and hydrolyzed RNA, marketed by Laboratoires Sérobiologiques under the trademark CPP LS 2633-12F®, the water-soluble fraction of corn marketed by Solabia under the trademark Phytovityl®, the mixture of extract of fumitory and of extract of lemon marketed under the trademark Unicotrozon C-49® by Induchem, and the mixture of extracts of ginseng, of apple, of peach, of wheat and of barley, marketed by Provital under the trademark Pronalen Bioprotect®.

As agents for trapping monocyclic or polycyclic aromatic compounds, which may be included in the compositions according to the invention, exemplary are in particular tannins such as ellagic acid; indole derivatives, in particular 3-indolecarbinol; extracts of tea, in particular of green tea, extracts of water hyacinth or *Eichornia crassipes*; and the water-soluble fraction of corn marketed by Solabia under the trademark Phytovityl®.

Finally, as heavy-metal-trapping agents that may be included in the compositions according to the invention, exemplary are in particular chelating agents such as EDTA, the pentasodium salt of ethylenediaminetetramethylenephosphonic acid, and N,N'-bis(3,4,5-trimethoxybenzyl) ethylenediamine or one of the salts, metal complexes or esters thereof; phytic acid; chitosan derivatives; extracts of tea, in particular of green tea; tannins such as ellagic acid; sulfur-containing amino acids such as cysteine; extracts of water hyacinth (*Eichornia crassipes*); and the water-soluble fraction of corn marketed by Solabia under the trademark Phytovityl®.

Advantageously, the compositions according to the invention contain at least one organic photoprotective agent and/or at least one mineral photoprotective agent that is active in the UV-A and/or UV-B range (absorbers), and that is water-soluble, liposoluble or insoluble in the common cosmetic solvents. Preferably, a system for screening out both UV-A radiation and UV-B radiation will be employed.

Sunscreens are molecules that absorb UV radiation and thus prevent it from reaching the skin cells. They can absorb either mainly UV-B or mainly UV-A, depending on their nature. There are two major categories of sunscreens, either organic, or mineral (zinc oxide or titanium oxide). By using them in cosmetic compositions in combination and in a sufficient amount, they can block a large proportion of the UV radiation.

However, it is commonly accepted that, to be effective, these formulations must be used under good application conditions (sufficient amount, frequent renewal and uniform spreading). These application conditions are not always adhered to by the user, which increases the risk of an appreciable amount of UV radiation reaching the skin cells, and thus of giving rise to the biological effects mentioned above. Furthermore, to obtain absorption with respect to all the wavelengths of the UV-B+UV-A solar UV spectrum, several molecules that absorb in complementary wavelength ranges need to be combined.

The additional organic screening agents are selected especially from anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives, especially those described in U.S. Pat. No. 5,624,663; benzimidazole derivatives; imidazolines; bis-benzazolyl derivatives as described in EP 669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB 2,303,549, DE 197,26,184 and EP 893,119; benzoxazole derivatives as described in EP 0,832,642, EP 1,027,883, EP 1,300,137 and DE 101,62,844; screening polymers and screening silicones such as those described especially in WO 93/04665; α-alkylstyrene-based dimers, such as those described in DE 198,55,649; 4,4-diarylbutadienes such as those described in EP 0,967,200, DE 197,46,654, DE 197,55,649, EP-A-1,008,586, EP1,133,980 and EP 133,981; merocyanin derivatives such as those described in WO 04/006,878, WO 05/058,269 and WO 06/032,741; and mixtures thereof.

As examples of additional organic photoprotective agents, exemplary are those denoted hereinbelow under their INCI name:

Cinnamic Derivatives:
Ethylhexyl methoxycinnamate marketed in particular under the trademark Parsol MCX by DSM Nutritional Products, Inc.,
Isopropyl methoxycinnamate,
Isoamyl methoxycinnamate marketed under the trademark Neo Heliopan E 1000 by Symrise,
DEA methoxycinnamate,
Diisopropyl methylcinnamate,
Glyceryl ethylhexanoate dimethoxycinnamate;
   para-Aminobenzoic Acid Derivatives:
PABA,
Ethyl PABA,
Ethyl dihydroxypropyl PABA,
Ethylhexyl dimethyl PABA marketed in particular under the trademark Escalol 507 by ISP,
Glyceryl PABA,
PEG-25 PABA marketed under the trademark Uvinul P25 by BASF;
   Salicylic Derivatives:
Homosalate marketed under the trademark Eusolex HMS by Rona/EM Industries,
Ethylhexyl salicylate marketed under the trademark Neo Heliopan OS by Symrise,
Dipropylene glycol salicylate marketed under the trademark Dipsal by Scher,
TEA salicylate marketed under the trademark Neo Heliopan TS by Symrise;
   β,β-Diphenylacrylate Derivatives:
Octocrylene marketed in particular under the trademark Uvinul N539 by BASF,
Etocrylene marketed in particular under the trademark Uvinul N35 by BASF;
   Benzophenone Derivatives:
Benzophenone-1 marketed under the trademark Uvinul 400 by BASF,
Benzophenone-2 marketed under the trademark Uvinul D50 by BASF,
Benzophenone-3 or Oxybenzone marketed under the trademark Uvinul M40 by BASF,
Benzophenone-4 marketed under the trademark Uvinul MS40 by BASF,
Benzophenone-5,
Benzophenone-6 marketed under the trademark Helisorb 11 by Norquay,
Benzophenone-8 marketed under the trademark SpectraSorb UV-24 by American Cyanamid, Benzophenone-9 marketed under the trademark Uvinul DS-49 by BASF,
Benzophenone-12
n-hexyl 2-(4-diethylamino-2-hydroxybenzoyl)benzoate marketed under the trademark Uvinul A+ by BASF;

Benzylidenecamphor Derivatives:
3-Benzylidenecamphor manufactured under the trademark Mexoryl SD by Chimex,
4-Methylbenzylidenecamphor marketed under the trademark Eusolex 6300 by Merck,
Benzylidenecamphorsulfonic acid manufactured under the trademark Mexoryl SL by Chimex,
Camphor benzalkonium methosulfate manufactured under the trademark Mexoryl SO by Chimex,
Terephthalylidenedicamphorsulfonic acid manufactured under the trademark Mexoryl SX by Chimex,
Polyacrylamidomethylbenzylidenecamphor manufactured under the trademark Mexoryl SW by Chimex;

Phenylbenzimidazole Derivatives:
Phenylbenzimidazolesulfonic acid marketed in particular under the trademark Eusolex 232 by Merck,
Disodium phenyl dibenzimidazole tetrasulfonate marketed under the trademark Neo Heliopan AP by Symrise;

Phenylbenzotriazole Derivatives:
Drometrizole trisiloxane marketed under the trademark Silatrizole by Rhodia Chimie,
Methylenebis(benzotriazolyl)tetramethylbutylphenol marketed in solid form under the trademark MIXXIM BB/100 by Fairmount Chemical, or in micronized form as an aqueous dispersion under the trademark Tinosorb M by Ciba Specialty Chemicals;

Triazine Derivatives:
Bis(ethylhexyloxyphenol)methoxyphenyltriazine marketed under the trademark Tinosorb S by Ciba Geigy, Ethylhexyltriazone marketed in particular under the trademark Uvinul T150 by BASF,
Diethylhexylbutamidotriazone marketed under the trademark Uvasorb HEB by Sigma 3V,
2,4,6-tris(diisobutyl 4'-aminobenzalmalonate)-s-triazine,
2,4,6-tris(dineopentyl 4'-aminobenzalmalonate)-s-triazine,
2,4-bis(n-butyl 4'-aminobenzoate)-6-(aminopropyltrisiloxane)-s-triazine,
2,4-bis(dineopentyl 4'-aminobenzalmalonate)-6-(n-butyl 4'-aminobenzoate)-s-triazine,
the symmetrical triazine screening agents described in U.S. Pat. No. 6,225,467, WO 2004/085,412 (see compounds 6 and 9) or the document Symmetrical Triazine Derivatives IP.COM Journal, IP.COM INC West Henrietta, N.Y., US (20 Sep. 2004), especially 2,4,6-tris(biphenyl)-1,3,5-triazines (in particular 2,4,6-tris(biphenyl-4-yl-1,3,5-triazine) and 2,4,6-tris(terphenyl)-1,3,5-triazine which is also described in Beiersdorf WO 06/035,000, WO 06/034,982, WO 06/034,991, WO 06/035,007, WO 2006/034,992 and WO 2006/034,985;

Anthranilic Derivatives:
Menthyl anthranilate marketed under the trademark Neo Heliopan MA by Haarmann and Reimer;

Imidazoline Derivatives:
Ethylhexyldimethoxybenzylidenedioxoimidazoline propionate;

Benzalmalonate Derivatives:
Polyorganosiloxane containing benzalmalonate functions, for instance Polysilicone-15, marketed under the trademark Parsol SLX by DSM Nutritional Products, Inc.;

4,4-Diarylbutadiene Derivatives:
1,1-Dicarboxy(2,2'-dimethylpropyl)-4,4-diphenylbutadiene;

Benzoxazole Derivatives:
2,4-bis[5-(1-dimethylpropyl)benzoxazol-2-yl(4-phenyl)imino]-6-(2-ethylhexyl)imino-1,3,5-triazine marketed under the trademark Uvasorb K2A by Sigma 3V;

Merocyanin Derivatives
Octyl 5-N,N-diethylamino-2-phenylsulfonyl-2,4-pentadienoate;
and mixtures thereof.

The preferential organic screening agents are selected from among:
Ethylhexyl methoxycinnamate,
Ethylhexyl salicylate,
Homosalate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methyl benzylidenecamphor,
Terephthalylidenedicamphorsulfonic acid,
Disodium phenyldibenzimidazoletetrasulfonate,
Methylenebis(benzotriazolyl)tetramethylbutylphenol,
Bis(ethylhexyloxyphenol)methoxyphenyltriazine,
Ethylhexyltriazone,
Diethylhexylbutamidotriazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,5-triazine,
Drometrizole trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine,
Octyl 5-N,N-diethylamino-2-phenylsulfonyl-2,4-pentadienoate,
and mixtures thereof.

The organic screening agents in accordance with the invention generally represent from 0.1% to 30% to preferably from 1% to 25% of the total weight of the composition.

The additional mineral UV screening agents used in accordance with the present invention are metal oxide pigments. More preferentially, the mineral UV screening agents of the invention are metal oxide particles with a mean elementary particle size of less than or equal to 500 nm, more preferentially from 5 nm and 500 nm, even more preferentially from 10 nm and 100 nm and preferentially from 15 nm and 50 nm.

They may be selected especially from among titanium, zinc, iron, zirconium or cerium oxides or mixtures thereof, and more particularly titanium oxides.

Such coated or uncoated metal oxide pigments are described in particular in EP-A-0,518,773. Commercial pigments that are exemplary include the products marketed by companies Kemira, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminum salts of fatty acids, metal alkoxides (of titanium or of aluminum), polyethylene, silicones, proteins (collagen, elastin), alkanolamines, silicon oxides, metal oxides or sodium hexametaphosphate.

The coated pigments are more particularly titanium oxides that have been coated:

with silica, such as the product Sunveil from the company Ikeda, with silica and iron oxide, such as the product Sunveil F from the company Ikeda, with silica and alumina, such as the products Microtitanium Dioxide MT 500 SA and Microtitanium Dioxide MT 100 SA from the company Tayca, Tioveil from the company Tioxide, with alumina, such as the products Tipaque TTO-55 (B) and Tipaque TTO-55 (A) from the company Ishihara and UVT 14/4 from the company Kemira, with alumina and aluminum stearate, such as the product Microtitanium Dioxide MT 100 TV, MT 100 TX, MT 100 Z and MT-01 from the company Tayca, and the products Solaveil CT-10 W and Solaveil CT 100 from the company Uniqema, and the product Eusolex T-AVO from the company Merck, with silica, alumina and alginic acid, such as the product MT-100 AQ from the company Tayca, with alumina and aluminum laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR 351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminum stearate and treated with a silicone, such as the product STT-30-DS from the company Titan Kogyo, with silica and treated with a silicone, such as the product UV-Titan X 195 from the company Kemira, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca, $TiO_2$ treated with octyltrimethylsilane, marketed under the trademark T 805 by Degussa Silices, $TiO_2$ treated with a polydimethylsiloxane, marketed under the trademark 70250 Cardre UF TiO2SI3 by Cardre, anatase/rutile $TiO_2$ treated with a polydimethylhydrogenosiloxane, marketed under the trademark Microtitanium Dioxide USP Grade Hydrophobic by Color Techniques.

The uncoated titanium oxide pigments are marketed, for example, by Tayca under the trademarks Microtitanium Dioxide MT 500 B or Microtitanium Dioxide MT 600 B, by Degussa under the trademark P 25, by Wackher under the trademark Transparent titanium oxide PW, by Miyoshi Kasei under the trademark UFTR, by Tomen under the trademark ITS and by Tioxide under the trademark Tioveil AQ.

The uncoated zinc oxide pigments are, for example:
those marketed under the trademark Z-Cote by Sunsmart;
those marketed under the trademark Nanox by Elementis;
those marketed under the trademark Nanogard WCD 2025 by Nanophase Technologies.

The coated zinc oxide pigments are, for example:
those marketed under the trademark Zinc Oxide CS-5 by Toshibi (ZnO coated with polymethylhydrogenosiloxane);
those marketed under the trademark Nanogard Zinc Oxide FN by Nanophase Technologies (as a 40% dispersion in Finsolv TN, $C_{12}$-$C_{15}$ alkyl benzoate);
those marketed under the trademark Daitopersion ZN-30 and Daitopersion ZN-50 by Daito (dispersions in cyclopolymethylsiloxane/oxyethylenated polydimethylsiloxane, containing 30% or 50% of nanozinc oxides coated with silica and polymethylhydrogenosiloxane);
those marketed under the trademark NFD Ultrafine ZnO by Daikin (ZnO coated with perfluoroalkyl phosphate and copolymer based on perfluoroalkylethyl as a dispersion in cyclopentasiloxane);
those marketed under the trademark SPD-Z1 by Shin-Etsu (ZnO coated with silicone-grafted acrylic polymer, dispersed in cyclodimethylsiloxane);
those marketed under the trademark Escalol Z100 by ISP (alumina-treated ZnO dispersed in an ethylhexyl methoxycinnamate/PVP-hexadecene/methicone copolymer mixture);
those marketed under the trademark Fuji ZnO-SMS-10 by Fuji Pigment (ZnO coated with silica and polymethylsilsesquioxane);
those marketed under the trademark Nanox Gel TN by Elementis (ZnO dispersed at a concentration of 55% in $C_{12}$-$C_{15}$ alkyl benzoate with hydroxystearic acid polycondensate).

The uncoated cerium oxide pigments are marketed under the trademark Colloidal Cerium Oxide by Rhone-Poulenc.

The uncoated iron oxide pigments are marketed, for example, by Arnaud under the trademarks Nanogard WCD 2002 (FE 45B), Nanogard Iron FE 45 BL AQ, Nanogard FE 45R AQ and Nanogard WCD 2006 (FE 45R) or by Mitsubishi under the trademark TY-220.

The coated iron oxide pigments are marketed, for example, by Arnaud under the trademarks Nanogard WCD 2008 (FE 45B FN), Nanogard WCD 2009 (FE 45B 556), Nanogard FE 45 BL 345 and Nanogard FE 45 BL or by BASF under the trademark Transparent Iron Oxide.

Also exemplary are mixtures of metal oxides, especially of titanium dioxide and of cerium dioxide, including the silica-coated equal-weight mixture of titanium dioxide and of cerium dioxide, marketed by Ikeda under the trademark Sunveil A, and also the alumina, silica and silicone-coated mixture of titanium dioxide and of zinc dioxide, such as the product M 261 marketed by Kemira, or the alumina, silica and glycerol-coated mixture of titanium dioxide and of zinc dioxide, such as the product M 211 marketed by Kemira.

According to the invention, coated or uncoated titanium oxide pigments are particularly preferred.

The mineral screening agents in accordance with the invention generally represent from 0.5% to 40% to preferably from 1% to 30% of the total weight of the composition.

The mineral screening agents may be introduced into the compositions according to the invention in their native form or in the form of a pigmentary paste, i.e., as a mixture with dispersants, as described, for example, in GB-A-2,206,339.

A vitamin E derivative that may especially be used is tocopheryl acetate.

The agents for stimulating DNA repair are especially enzymes that promote its repair, such as photolyase and/or endonuclease T4.

The compositions may also contain moisturizers, NO-synthase inhibitors, free-radical scavengers or agents for stimulating the synthesis of epidermal macromolecules and/or for preventing their degradation.

The amounts of these various components are easily adapted by one person skilled in the art.

To further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES OF SYNTHESIS

Example 1

Synthesis of 4-methyl-1,2-dithiolane-4-carboxylic acid (Compound 1)

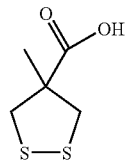

8 g of dichloropivalic acid are placed in a 250 ml three-necked flask on which are mounted a condenser and a dropping funnel. The acid is dissolved in 80 ml of water, and 4.6 g of $Na_2CO_3$ are slowly added. A solution of 10.7 g of potassium thioacetate is added dropwise, and the reaction medium is brought to reflux. 14.9 g of $Na_2CO_3$ are added and the medium is again refluxed. After disappearance of the starting material, 7.3 ml of DMSO are added, followed by refluxing. The dithiolane is obtained after acidification by precipitating and drying the solid under vacuum.

1H NMR (400 MHz, DMSO-d6): δ ppm 3.69 (d, 2H), 2.95 (d, 2H), 1.53 (s, 3H), ESI–:
[(M, H)–]=163 m/z

Example 2

Synthesis of octyl 4-methyl-1,2-dithiolane-4-carboxylate (Compound 9)

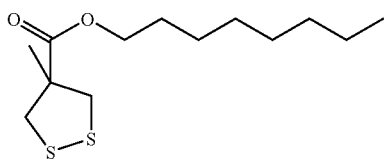 [SMILES: CCCCCCCCOC(=O)C1(C)CSSC1]

1 g of acid (24) and then 0.8 ml of 1-chloro-N,N,2-trimethyl-propenylamine (27) are placed in 20 ml of dichloromethane in a 100 ml three-necked flask using a syringe. The mixture is stirred for 1 hour, followed by dropwise addition via an additional funnel to a reaction medium at −5° C. containing 1.28 ml of triethylamine, 0.96 ml of octanol and 20 ml of dichloromethane. The mixture is stirred. The reaction medium is then washed with water (3×30 ml). The aqueous phase is extracted with 3×10 ml of EtOAc. The combined organic phases are washed with 30 ml of saturated aqueous NaCl solution and then dried over $Na_2SO_4$, filtered and then concentrated under vacuum (500 mbar, T=40° C.) on a rotavapor. The crude product obtained is a yellow oil (m=1.25 g). Purification is performed by flash chromatography on a column of silica (m $SiO_2$=40 g, eluting with a 100/0 and then 98/2 heptane/EtOAc gradient).

After concentrating the fractions on a rotavapor (P=100 mbar, T=40° C.), 1.08 g of pure expected product are obtained.

Yellow oil; yield=66%; Rf (ester)=0.16 (eluent: cyclohexane);

1H NMR (400 MHz, DMSO-d6): δ ppm 4.08 (t, 2H), 3.57 (d, 2H), 3.02 (d, 2H), 1.58 (m, 2H), 1.40 (s, 3H), 1.29 (m, 10H), 0.86 (t, 3H)

MS m/z (M+, 277; M+23, 299)

The following manipulations were carried out under the same conditions described previously, with only the nucleophile varying.

Example 3

Synthesis of S-[2-(acetylamino)ethyl]4-methyl-1,2-dithiolane-4-carbothioate (Compound 13)

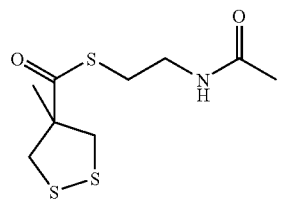

Method identical to that of Example 2: the nucleophile used is N-acetylcysteamine (0.64 ml).

Purification is performed by flash chromatography on a column of silica (m $SiO_2$=40 g; eluting with a linear gradient of 100/0 and then 98/2 DCM/MeOH.)

After concentrating the fractions on a rotavapor (P=200 mbar, T=40° C.), 0.32 g of a mixture of the expected product with N,N,2-trimethylpropionamide (28) is obtained.

Thick yellow liquid, yield=10%; Rf (expected)=0.3; eluent: 95/5 DCM/MeOH; 1H NMR (DMSO-d6): δ ppm 8.03 (t, NH), 3.57 (d, 2H), 3.18 (dt 2H), 3.10 (d, 2H), 2.96 (m, 2H), 1.79 (s, 3H), 1.43 (s, 3H); MS m/z (M+, 266; M+23, 288)

Example 4

Synthesis of N-(2-hydroxyethyl)-4-methyl-1,2-dithiolane-4-carboxamide (Compound 14)

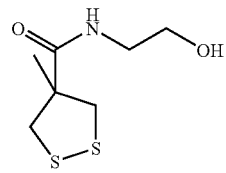

Method identical to that of Example 2: the nucleophile used is ethanolamine (0.36 ml). After filtering the reaction medium, a crude yellow oil is obtained (m=1.850 g)

Purification is performed by flash chromatography on a column of silica (eluting with a linear gradient of 100/0 and then 98/2 DCM/MeOH.

After concentrating the fractions on a rotavapor (P=500 mbar, T=40° C.), 800 mg of pure expected yellow oil are obtained; yield=65%.

Rf (expected)=0.43; eluent: 9/1 DCM/MeOH;

1H NMR (DMSO-d6): δ ppm 7.80 (t, NH), 4.64 (t, OH), 3.53 (d, 2H), 3.40 (dt, 2H), 3.14 (m, 2H), 2.99 (d, 2H), 1.34 (s, 3H); MS m/z (M+, 208; M+23, 230)

Example 5

Synthesis of 4-methyl-1,2-dithiolane-4-carboxamide (Compound 2)

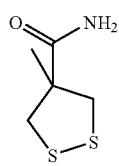

Method (Ex. 5-a) identical to that of Example 2: the nucleophile used is ammonia in isopropanol (9.5 ml). After filtering the reaction medium, a crude yellow oil is obtained (m=1.853 g).

Purification is performed by flash chromatography on a column of silica (eluent: DCM).

After concentrating the fractions on a rotavapor (P=600 mbar, T=40° C.), 500 mg of pure expected yellow solid are obtained. Yield=52%.

Alternatively, method (Ex. 5-b), 1.3 equivalents of isobutyl chloroformate are added, at 0° C., to a solution of 1 g of compound 1 in THF with 1.2 equivalents of triethylamine. After 2 hours at room temperature, the reaction medium is added to a cooled solution of ammonia, either at 28% in water or at 2N in isopropanol. The medium is stirred at room temperature for the time required, and then concentrated under vacuum. The crude product is then taken up in toluene, to give compound 2 after precipitation.

Yield=60%

Rf (expected)=0.45; eluent: 95/5 DCM/MeOH; 1H NMR (DMSO-d6): δ ppm 7.38 (s, NH), 7.13 (s, NH), 3.53 (d, 2H), 2.97 (d, 2H), 1.34 (s, 3H); ESI–: [(M, H)–]=162 m/z; ESI+: [(M, Na)+]=186 m/z; ESI+: [(M, H)+]=164 m/z;

ESI+: [(M, Na, MeOH)+]=218 m/z

Example 6

Synthesis of N-(2,3-dihydroxypropyl)-4-methyl-1,2-dithiolane-4-carboxamide (Compound 15)

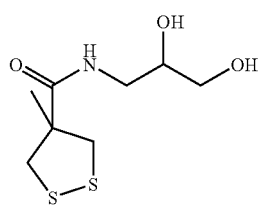

Method identical to that of Example 2: the amount of starting acid used is 0.25 g and the nucleophile used is dimethyldioxalanemethanamine (0.2 ml).

110 mg of pure expected yellow oil are obtained. Yield=26% Rf (expected)=0.51; eluent: 95/5 DCM/MeOH; 1H NMR (DMSO-d6): δ ppm 7.77 (t, 1H: NH), 3.55 (dd 4H, H3: diastereoisomers), 3.5 (m, 4H, H7: diastereoisomers), 3.20 (m, 2H, H8: diastereoisomers), 3.05 (dd, 2H: H9 and H9'), 2.99 (dd, 4H, H5), 1.35 (s, 12H, H10+H11: diastereoisomers), 0.9 (d, 3H, H6); MS m/z (M+23, 300)

70 mg of the pure product protected in acetonide form and about 5 g of Dowex resin are used in a solution of 3 ml of water and 2 ml of THF. The reaction mixture is stirred at room temperature for 20 hours and then at 40° C. for 40 hours.

The reaction medium with the resin is filtered under vacuum and washed with 3×10 ml of water and then 2×10 ml of EtOH. The filtrate is then concentrated on a rotavapor (P=200 mbar, T=40° C.). 30 mg of a yellow oil containing two diastereoisomers are obtained.

Rf (expected)=0.24; eluent: 9/1 DCM/MeOH; 1H NMR (DMSO-d6): δ ppm 7.80 (t, 1H: NH), 4.73 (d, OH), 4.50 (t, OH), 3.55 (d, 4H), 3.4 (m, 2H), 3.2 (m, 1H), 3.1 (m, 2H), 2.99 (d, 4H), 1.35 (s, 3H); MS m/z (M+, 208; M+23, 230)

Example 7

Synthesis of N-heptyl-4-methyl-1,2-dithiolane-4-carboxamide (Compound 10)

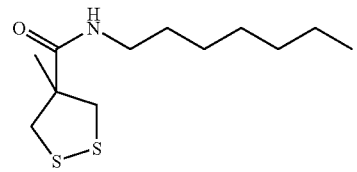 [SMILES: CCCCCCCNC(=O)C1(C)CSSC1]

Method identical to that of Example 2: the nucleophile is 0.22 ml of n-heptylamine.

The crude product obtained is a yellowish oil (m=0.27 g).

Purification is performed by flash chromatography on a column of silica (m $SiO_2$=12 g; eluent: 99/1 DCM/MeOH)

After concentrating the fractions on a rotavapor (P=500 mbar, T=40° C.), 0.21 g of pure expected yellow oil is obtained. Yield=54%.

Rf (expected)=0.5; eluent: 99/1 DCM/MeOH; 1H NMR (DMSO-d6): δ ppm 7.78 (t, NH), 3.53 (d, 2H), 3.1 (dt, 2H), 2.97 (d, 2H), 1.41 (tt, 2H), 1.34 (s, 3H), 1.23 (m, 8H), 0.85 (t, 3H); MS m/z (M+, 262; M+23, 284)

Example 8

Synthesis of methyl 2-{[(4-methyl-1,2-dithiolan-4-yl)carbonyl]amino}-4-(methylsulfanyl)butanoate (Compound 12)

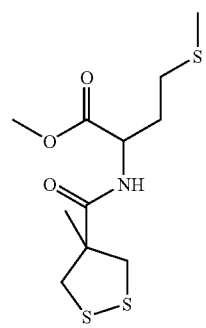

Method identical to that of Example 2: the nucleophile is L-methionine methyl ester.

1H NMR (DMSO-d6): δ ppm 8.13 (d, NH), 4.4 (m, 1H), 3.63 (s, 3H), 3.58 (m, 2H), 3.02 (m, 2H), 2.5 (m, 2H), 2.04 (s, 3H), 1.96 (m, 2H), 1.38 (s, 3H); MS m/z (M+, 310; M+23, 332)

Example 9

Synthesis of N-butyl-4-methyl-1,2-dithiolane-4-carboxamide (Compound 11)

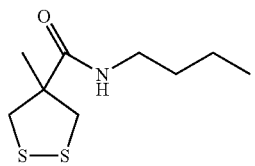

equivalents of triethylamine and 1 equivalent of diethyl cyanophosphate are added to 1 g of 1,2-dithiolane-4-methyl-4-carboxylic acid in ml of anhydrous THF, at 0° C. 1.1 equivalents of n-butylamine are added at 0° C. and the medium is stirred for 1 hour while warming to room temperature. After evaporation and aqueous work-up by extraction, the concentrated crude reaction product is purified on a column of silica (eluent: dichloromethane). After evaporating off the fractions of interest, a yellow oil is obtained.

1H NMR (DMSO-d6): δ ppm 7.79 (t, NH), 3.53 (d, 2H), 3.1 (dt, 2H), 2.97 (d, 2H), 1.41 (tt, 2H), 1.34 (s, 3H), 1.23 (m, 8H), 0.85 (t, 3H); MS m/z (M+, 262; M+23, 284)

1H NMR (DMSO-d6): δ ppm 7.79 (t, NH), 3.54 (d, 2H), 3.08 (dt, 2H), 2.98 (d, 2H), 1.40 (q, 2H), 1.34 (s, 3H), 1.27 (m, 4H), 0.87 (t, 3H); ESI+: [(M, Na)+]=242 m/z Example 10

Synthesis of 4-methyl-1,2-dithiolane-4-carboxylic acid 1-oxide (Compound 23)

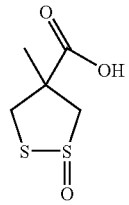

1 equivalent of aqueous 30% hydrogen peroxide solution is added to 100 mg of 4-methyl-1,2-dithiolane-4-carboxylic acid in 2 ml of acetone. The reaction medium is stirred at 20° C. overnight. After concentrating under vacuum, the thiosulfinate is obtained qualitatively in the form of a white solid as a mixture of two diastereoisomers in proportions of 70/30.

1H NMR (DMSO-d6): δ ppm
major diastereoisomer: 4.38 (d, 1H), 3.78 (q, 2H), 3.11 (d, 1H), 1.57 (s, 3H)
minor diastereoisomer: 4.36 (d, 1H), 3.96 (d, 1H), 3.42 (d, 1H), 3.31 (d, 1H), 1.51 (s, 3H)

13C NMR (DMSO-d6): δ ppm: 174.95; 174.63; 71.96; 70.85; 58.98; 56.73; 46.53; 45.03; 23.77; 21.96

ESI−: [(M, H)−]=179 m/z

Example 11

Synthesis of 4-methyl-1,2-dithiolane-4-carboxylic acid 1,1-dioxide (Compound 24)

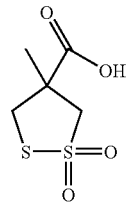

2 equivalents of aqueous 30% hydrogen peroxide solution and 0.15 equivalent of sodium tungstate $Na_2WO_4$ are added to 100 mg of 4-methyl-1,2-dithiolane-4-carboxylic acid in 2 ml of acetone. The reaction medium is stirred at 20° C. overnight. After filtering and concentrating under vacuum, the crude product is purified on a column of silica to give the thiosulfonate in the form of a white solid.

1H NMR (DMSO-d6): δ ppm 4.14 (d, 1H), 4.05 (d, 1H), 3.69 (d, 1H), 3.66 (d, 1H), 1.51 (s, 3H);

13C NMR (DMSO-d6): δ ppm 173.90; 65.86; 50.26; 44.58; 23.59

ESI−: [(M, H)−]=195 m/z

Example 12

Synthesis of 4-methyl-1,2-dithiolane-4-carboxylic acid 1,1,2,2-tetroxide (Compound 28)

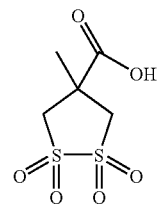

4 equivalents of aqueous 30% hydrogen peroxide solution and 4 equivalents of sodium tungstate $Na_2WO_4$ are added to 100 mg of 4-methyl-1,2-dithiolane-4-carboxylic acid in 2 ml of acetone. The reaction medium is stirred at 20° C. overnight. After filtering and concentrating under vacuum, the cyclic disulfone is obtained in the form of a white solid.

1H NMR (DMSO-d6): δ ppm 3.16 (d, 2H), 2.97 (d, 2H), 1.4 (s, 3H);

13C NMR (DMSO-d6): δ ppm 176.31; 58.06; 43.76; 20.62

ESI−: [(M, H)−]=227 m/z

Example 13

Synthesis of ethyl 4-methyl-1,2-dithiolane-4-carboxylate (Compound 4)

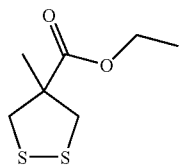

Sulfonic resin Dowex 50 WX8 (marketed by Aldrich) is added to 1 g of 4-methyl-1,2-dithiolane-4-carboxylic acid in 20 ml of ethanol. The mixture is refluxed for 24 hours and then filtered and evaporated to give the pure ethyl ester.

1H NMR (DMSO-d6): δ ppm 4.13 (q, 2H), 3.58 (d, 2H), 3.02 (d, 2H), 1.40 (s, 3H), 1.20 (t, 3H)
ESI+: [(2M, Na)+]=407 m/z

Example 14

Synthesis of ethyl 4-methyl-1,2-dithiolane-4-carboxylate 1-oxide (Compound 25)

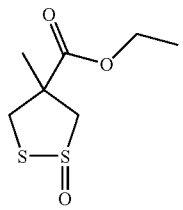

Oxidation of the ethyl ester is performed in the same manner as for the acid.

1H NMR (DMSO-d6): δ ppm
major diastereoisomer: 4.4 (d, 1H), 4.11 (q, 2H), 3.8 (d, 1H), 3.75 (d, 1H), 3.17 (d, 1H), 1.59 (s, 3H), 1.53 (t, 3H)
minor diastereoisomer: 4.2 (d, 1H), 4.11 (q, 2H), 3.98 (d, 1H), 3.8 (d, 1H), 3.42 (d, 1H), 3.32 (d, 1H), 1.51 (s, 3H)
13C NMR (DMSO-d6): δ ppm 174.95, 174.63, 71.96, 70.85, 58.98, 56.73, 46.53, 45.03, 23.77, 21.96
ESI+: [(M, Na)+]=231 m/z; ESI+: [(M, Na, MeOH)+]=263 m/z; ESI+: [(2M, Na)+]=439 m/z
ESI+: [(M, Na)+]=231 m/z; ESI+: [(M, Na, MeOH)+]=263 m/z; ESI+: [(2M, Na)+]=439 m/z

Example 15

Synthesis of 4-methyl-1,2-dithiolane-4-carboxamide 1-oxide (Compound 26)

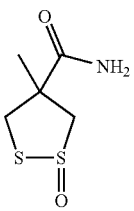

1 equivalent of aqueous 30% hydrogen peroxide solution is added to 100 mg of 4-methyl-1,2-dithiolane-4-carboxamide in 2 ml of acetone. The reaction medium is stirred at 20° C. overnight. After concentrating under vacuum and purifying on a column of silica, the thiosulfinate is obtained in the form of a white solid as a mixture of two diastereoisomers.

1H NMR (DMSO-d6): δ ppm
major diastereoisomer: 7.40 (bd, 2H), 4.31 (d, 1H), 3.78 (bs, 2H), 3.04 (d, 1H), 1.49 (s, 3H)
minor diastereoisomer: 7.32 (bd, 2H), 4.21 (d, 1H), 3.92 (d, 1H), 3.42 (d, 1H), 3.34 (d, 1H), 1.40 (s, 3H)
ESI−: [(M, H)−]=178 m/z

Example 16

Synthesis of 4-methyl-1,2-dithiolane-4-carboxamide 1,1-dioxide (Compound 27)

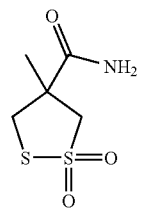

2 equivalents of aqueous 30% hydrogen peroxide solution and 0.15 equivalent of sodium tungstate $Na_2WO_4$ are added to 100 mg of 4-methyl-1,2-dithiolane-4-carboxamide in 2 ml of acetone. The reaction medium is stirred at 20° C. overnight. After filtering and concentrating under vacuum, the crude product is purified on a column of silica to give the thiosulfonate in the form of a white solid.

1H NMR (DMSO-d6): δ ppm 7.50 (bd, 2H), 4.21 (d, 1H), 4.08 (d, 1H), 3.66 (d, 1H), 3.59 (d, 1H), 1.49 (s, 3H);
ESI−: [(M, H)−]=194 m/z

Example 17

Synthesis of N-(4-hydroxy-3-methoxybenzyl)-4-methyl-1,2-dithiolane-4-carboxamide (Compound 16)

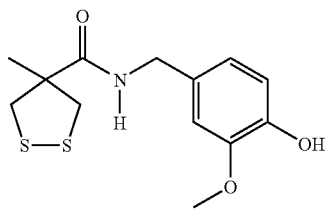 [SMILES: COc1cc(CNC(=O)C2(C)CSSC2)ccc1O]

24.3 mmol of N-hydroxysuccinimide are added to 24.3 mmol of dithiolane acid dissolved in 60 ml of dichloromethane cooled to 0° C. (on an ice bath). The reaction medium is stirred for 30 minutes at 0° C. A solution of 24.3 mmol of DCC in 50 ml of dichloromethane is added and the mixture is then stirred at 20° C. for 4 hours. The reaction medium is filtered and washed, and the filtrate is then evaporated to dryness on a rotavapor at 40° C. under vacuum to give 1-{[(4-methyl-1,2-dithiolan-4-yl)carbonyl]oxy}pyrrolidine-2,5-dione (m=7 g, quantitative yield). 10 mg of MeTHF, 3.16 mmol) of 4-(aminomethyl)-2-methoxyphenol hydrochloride and 3.16 mmol of triethylamine are added to 1.58 mmol of 1-{[(4-methyl-1,2-dithiolan-4-yl)carbonyl]oxy}pyrrolidine-2,5-dione. After stirring overnight, the mixture is filtered, rinsed with MeTHF and then evaporated. Flash chromatography, eluting with 98/2 dichloromethane/methanol, gives compound 16 in the form of a yellow oil (84% yield).

1H NMR (DMSO-d6): δ ppm 1.39 (s, 3H); 3.03 (d, 2H); 3.56 (d, 2H), 3.63 (s, 3H, OCH$_3$), 4.21 (d, 2H), 6.64 (dd, 1H, Ar), 6.69 (d, 1H, Ar), 6.80 (d, 1H, Ar), 8.31 (t, 1H, NH), 8.79 (s, 1H, OH)

ESI+: [(M, H)+]=300 m/z

Example 18

Synthesis of N-[2-(4-hydroxy-3-methoxyphenyl)ethyl]-4-methyl-1,2-dithiolane-4-carboxamide (Compound 17)

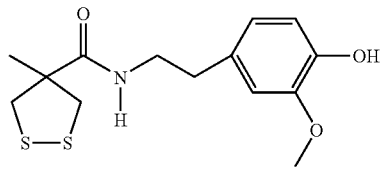

Same method as for compound 16 with 4-(2-aminoethyl)-2-methoxyphenol hydrochloride. Yellow oil; yield=64%

1H NMR (DMSO-d6): δ ppm 1.31 (s, 3H); 2.63 (t, 2H), 2.97 (d, 2H); 3.24 (m, 2H, NCH$_2$) 3.53 (d, 2H), 3.75 (s, 3H, OCH$_3$), 6.57 (dd, 1H, Ar), 6.67 (d, 1H, Ar), 6.74 (d, 1H, Ar), 8.86 (t, 1H, NH), 8.67 (s, 1H, OH)

ESI+: [(M, H)+]=314 m/z

Example 19

Synthesis of N,N-diethyl-4-methyl-1,2-dithiolane-4-carboxamide (Compound 18)

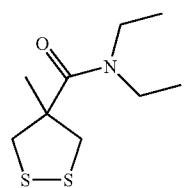

5 ml of anhydrous dichloromethane and 0.1 ml of anhydrous DMF are added to 2.26 mmol of compound 1. The mixture is cooled to 0° C. and 2.7 mmol of oxalyl chloride are added. The mixture is stirred at 20° C. and then added at 0° C. to a mixture of 2.26 mmol of diethylamine, 5 ml of anhydrous dichloromethane and 6.8 mmol of diisopropylethylamine. The reaction medium is stirred for 3 hours at 20° C. When the reaction is complete, the medium is diluted in 50 ml of dichloromethane and then washed with 2×30 ml of water and 1×50 ml of saturated NH$_4$Cl solution, dried over Na$_2$SO$_4$ and evaporated to dryness on a rotavapor. After flash chromatography (eluent: heptane/EtOAc), compound 18 is isolated in the form of a yellow oil (48% yield).

1H NMR (DMSO-d6): δ ppm 1.36 (s, 3H); 3.15 (d, 2H); 3.50 (d, 2H), 3.3 (m, 2×2H), 1.07 (m, 2×3H)

ESI+: [(M, H)+]=220 m/z

Example 20

Synthesis of methyl 2-(acetylamino)-3-{[(4-methyl-1,2-dithiolan-4-yl)carbonyl]sulfanyl}propanoate (Compound 19)

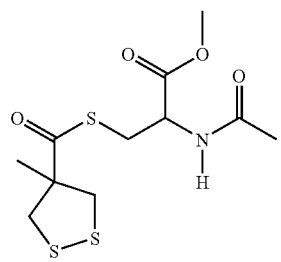 [SMILES: COC(=O)C(CSC(=O)C1(C)CSSC1)NC(C)=O]

Same method as in Example 19 with N-acetylcysteine methyl ester.

Yellow oil; yield=12%

1H NMR (DMSO-d6): δ ppm 1.42 (s, 3H); 1.84 (s, 3H, OCH$_3$); 3.15 (d, 2H); 3.56 (d, 2H), 3.38-3.12 (dd, 2H), 3.65 (s, 3H, COCH$_3$), 8.42 (d, 1H, NH)

ESI+: [(M, H)+]=324 m/z

Example 21

Synthesis of S-(2-hydroxyethyl) 4-methyl-1,2-dithiolane-4-carbothioate (Compound 20)

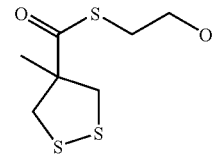

Same method as in Example 19 with sulfanylethanol.

Yellow oil; yield=26%

1H NMR (DMSO-d6): δ ppm 1.43 (s, 3H); 3.1 (d, 2H); 3.56 (d, 2H), 2.99 (t, 2H: CH$_2$S), 3.48 (q, 2H: CH$_2$OH)

ESI+: [(M, Na)+]=247 m/z

Example 22

Synthesis of ethyl {[(4-methyl-1,2-dithiolan-4-yl)carbonyl]sulfanyl}acetate (Compound 21)

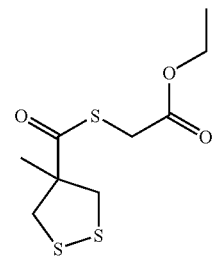

Same method as in Example 17 with ethyl thioglycolate.

Colorless oil; yield=7%

1H NMR (DMSO-d6): δ ppm 1.53 (s, 3H); 1.28 (t, 3H), 2.99 (d, 2H); 3.65 (d, 2H), 3.71 (s, 2H, SCH$_2$), 4.20 (q, 2H

Example 23

Synthesis of [(4-methyl-1,2-dithiolan-4-yl)carbonyl]pyrrolidine (Compound 22)

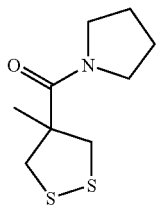

Same method as for Example 5-b with pyrrolidine.
Yellow solid; yield=38%
1H NMR (DMSO-d6): δ ppm 1.36 (s, 3H); 1.81 (m, 2×2H); 3.10 (d, 2H); 3.30 (m, 2×2H); 3.58 (d, 2H),
ESI+: [(M, H)+]=218 m/z

Example 24

Synthesis of 4-methyl-N-(1-methylethyl)-1,2-dithiolane-4-carboxamide (Compound 29)

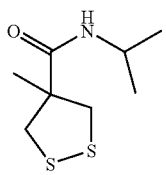

Same method as in Example 19 with isopropylamine.
Beige-colored solid; yield=54%
1H NMR (DMSO-d6): δ ppm 1.06 (d, 2×3H); 1.33 (s, 3H, Hc); 2.99 (d, 2H, Hb); 3.56 (d, 2H, Ha); 3.88 (m, 1H),
ESI+: [(M, H)+]=206 m/z

Example 25

Synthesis of 4-methyl-N-phenyl-1,2-dithiolane-4-carboxamide (Compound 30)

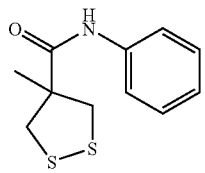

Same method as in Example 19 with aniline.
Yellow oil; yield=70%
1H NMR (DMSO-d6): δ ppm 1.51 (s, 3H, Hc); 2.99 (d, 2H, Hb); 3.75 (d, 2H, Ha), 7.08 (t, 1H, Ar), 7.3 (t, 2H, Ar), 7.60 (d, 2H, Ar), 9.56 (s, 1H, NH)
ESI+: [(M, H)+]=240 m/z

Example 26

Measurement of the Activity of the Compounds According to the Invention with Respect to Increasing the Level of GSH The study consisted in evaluating at the cellular level the protective effect of the reference molecule, lipoic acid, and also of lipoic acid derivatives according to the invention, with respect to the UV-DL-induced depletion of intracellular GSH.

To do this, HaCaT cells were exposed to UV daylight (UV-DL). The level of intracellular GSH was then measured, thus allowing evaluation of the possible protection afforded by the addition to the culture medium of the lipoic acid derivatives according to the invention.

UV daylight corresponds to the radiation of non-zenithal sunlight and to an average spectral illumination: it stimulates the radiation received by the skin of an individual in the course of a day and not solely to that corresponding to exposure to zenithal sunlight. Devices for reproducing this radiation are described in FR 2,863,356. The evaluation technique uses a fluorescent probe, monochlorobimane (MCB). MCB has the particular feature of having, unlike other bimane compounds such as monobromobimane, more selective reactivity towards glutathione: the blue fluorescent compound measured (GSH-monochlorobimane) results from an enzymatic reaction catalyzed by glutathione-S-transferase. The specificity of MCB towards GSH in our keratinocyte model (HaCaT line) was confirmed previously. Pretreatment of cells with the reference molecule, lipoic acid, for 24 hours at 1 mM affords approximately 100% protection against the UV-DL-induced depletion of GSH (see FIG. 1 showing the evaluation of the protective effect of lipoic acid at 1 mM in the MCB test on HaCaT: the measurement of the level of intracellular GSH is performed on keratinocytes that are or are not pretreated with lipoic acid at 1 mM and exposed to UV-DL at t=0, t=6 hours and t=24 hours after the exposure to UV-DL); this protection is about 83% at 500 μM and about 10% at 100 μM.

The following dithiolane compounds of the invention were tested:
4-methyl-1,2-dithiolane-4-carboxylic acid (compound 1)
octyl 4-methyl-1,2-dithiolane-4-carboxylate (compound 9)
N-heptyl-4-methyl-1,2-dithiolane-4-carboxamide (compound 10)
4-methyl-1,2-dithiolane-4-carboxamide (compound 2)
S-[2-(acetylamino)ethyl]4-methyl-1,2-dithiolane-4-carbothioate (compound 13)
N-(2-hydroxyethyl)-4-methyl-1,2-dithiolane-4-carboxamide (compound 14)
methyl 2-{[(4-methyl-1,2-dithiolan-4-yl)carbonyl]amino}-4-(methylsulfanyl)butanoate (compound 12)
4-methyl-1,2-dithiolane-4-carboxylic acid 1,1-dioxide (compound 24)
4-methyl-1,2-dithiolane-4-carboxamide 1-oxide (compound 26)
4-methyl-1,2-dithiolane-4-carboxamide 1,1-dioxide (compound 27).

Evaluation of the protective effect of compound 1 at 100 μM and at 30 μM of compounds 9, 10, 2, 13, 14, 12, 24, 26 and 27 is performed in the MCB test on HaCaT: evaluation of the protective effect of the silyl dithiolane compounds of WO 2008/058 999 at 100 μM is also performed in the MCB test on HaCaT: the compound 5-(1,2-dithiolan-3-yl)-N-[3-(trimethylsilyl)propyl]pentanamide and the compound (trimethylsilyl)methyl 5-(1,2-dithiolan-3-yl)pentanoate. Measurement of the intracellular level of GSH is performed on keratinocytes that have or have not been pretreated with the active agents and exposed to UV-DL, t=6 hours after the exposure to UV-DL). The results are given in the graphs in FIGS. 2 and 3.

| Active agent | % fluo | ET fluo | % protection |
|---|---|---|---|
| 4-methyl-1,2-dithiolane-4-carboxylic acid (compound 1) 100 μM | 88% | 4.39% | 74% |
| 4-methyl-1,2-dithiolane-4-carboxamide (compound 2) 30 μM | 92% | 23.58% | 86% |
| octyl 4-methyl-1,2-dithiolane-4-carboxylate (compound 9) 30 μM | 80% | 27.21% | 66% |
| N-heptyl-4-methyl-1,2-dithiolane-4-carboxamide (compound 10) 30 μM | 99% | 30.60% | 98% |
| methyl 2-{[(4-methyl-1,2-dithiolan-4-yl)carbonyl]amino}-4-(methylsulfanyl)butanoate (compound 12) 30 μM | 78% | 12.79% | 61% |
| S-[2-(acetylamino)ethyl]-4-methyl-1,2-dithiolane-4-carbothioate (compound 13) 30 μM | 71% | 2.39% | 50% |
| N-(2-hydroxyethyl)-4-methyl-1,2-dithiolane-4-carboxamide (compound 14) 30 μM | 78% | 2.79% | 61% |
| 4-methyl-1,2-dithiolane-4-carboxylic acid 1,1-dioxide (compound 24) 30 μM | 91% | 6.19% | 63% |
| 4-methyl-1,2-dithiolane-4-carboxamide 1-oxide (compound 26) 30 μM | 117% | 6.64% | 169% |
| 4-methyl-1,2-dithiolane-4-carboxamide 1-oxide (compound 26) 30 μM | 117% | 6.64% | 169% |
| 4-methyl-1,2-dithiolane-4-carboxamide 1,1-dioxide (compound 27) 30 μM | 100% | 3.85% | 101% |
| lipoic acid 100 μM (outside the invention) | 63% | 5.20% | 13% |
| (trimethylsilyl)methyl 5-(1,2-dithiolan-3-yl)pentanoate 100 μM according to WO 2008/058 999 (outside the invention) | 76% | 12.00% | 42% |
| 5-(1,2-dithiolan-3-yl)-N-[3-(trimethylsilyl)propyl]pentanamide 100 μM according to WO 2008/058 999 (outside the invention) | 75% | 10.50% | 41% |

Figure 2:
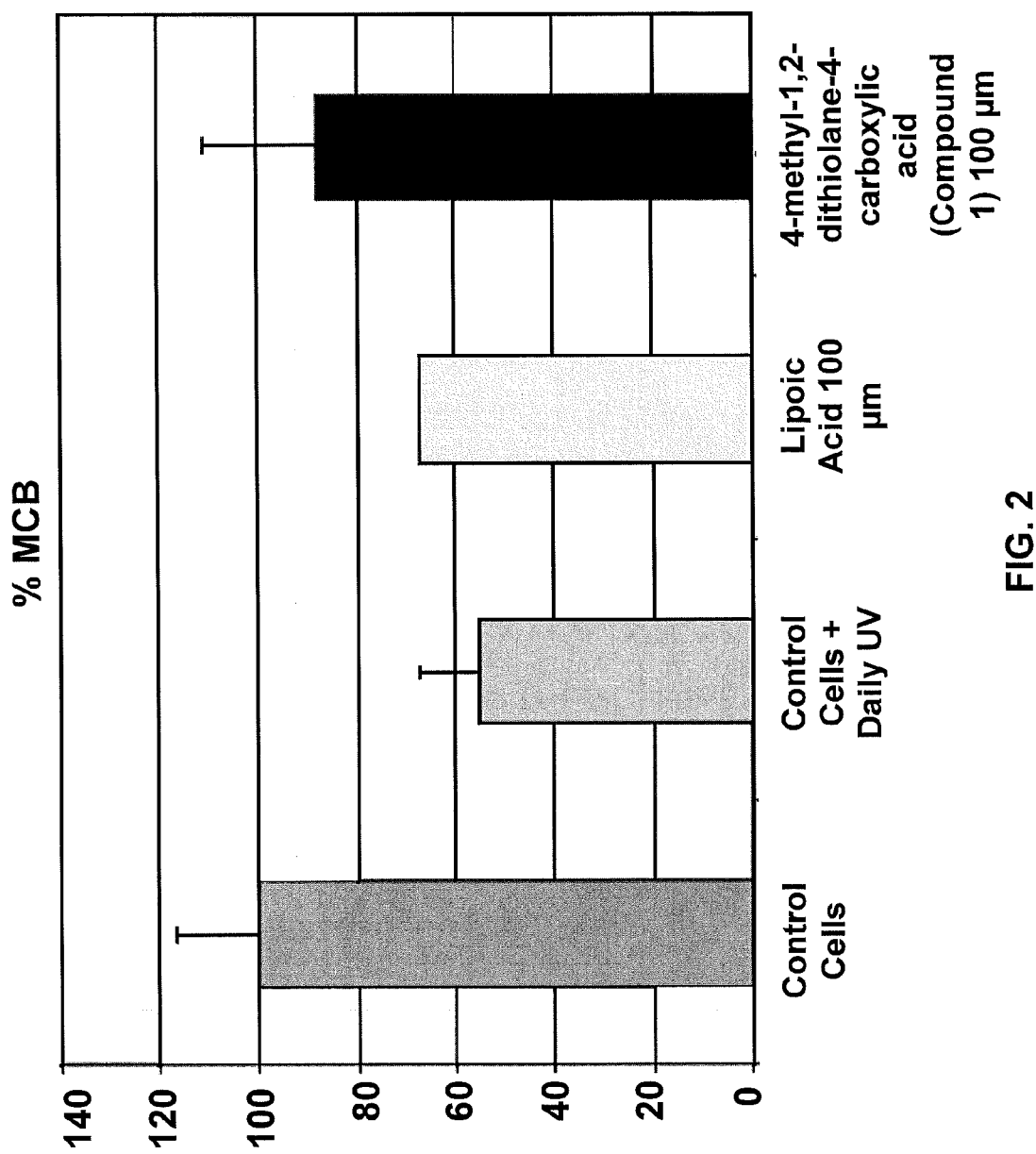
FIGS. 2 and 3 are graphs showing measurement of the intracellular level of GSH conducted on keratinocytes that either have or have not been pretreated with the active agents according to the invention and thereafter exposed to UV-DL.
Figure 3:
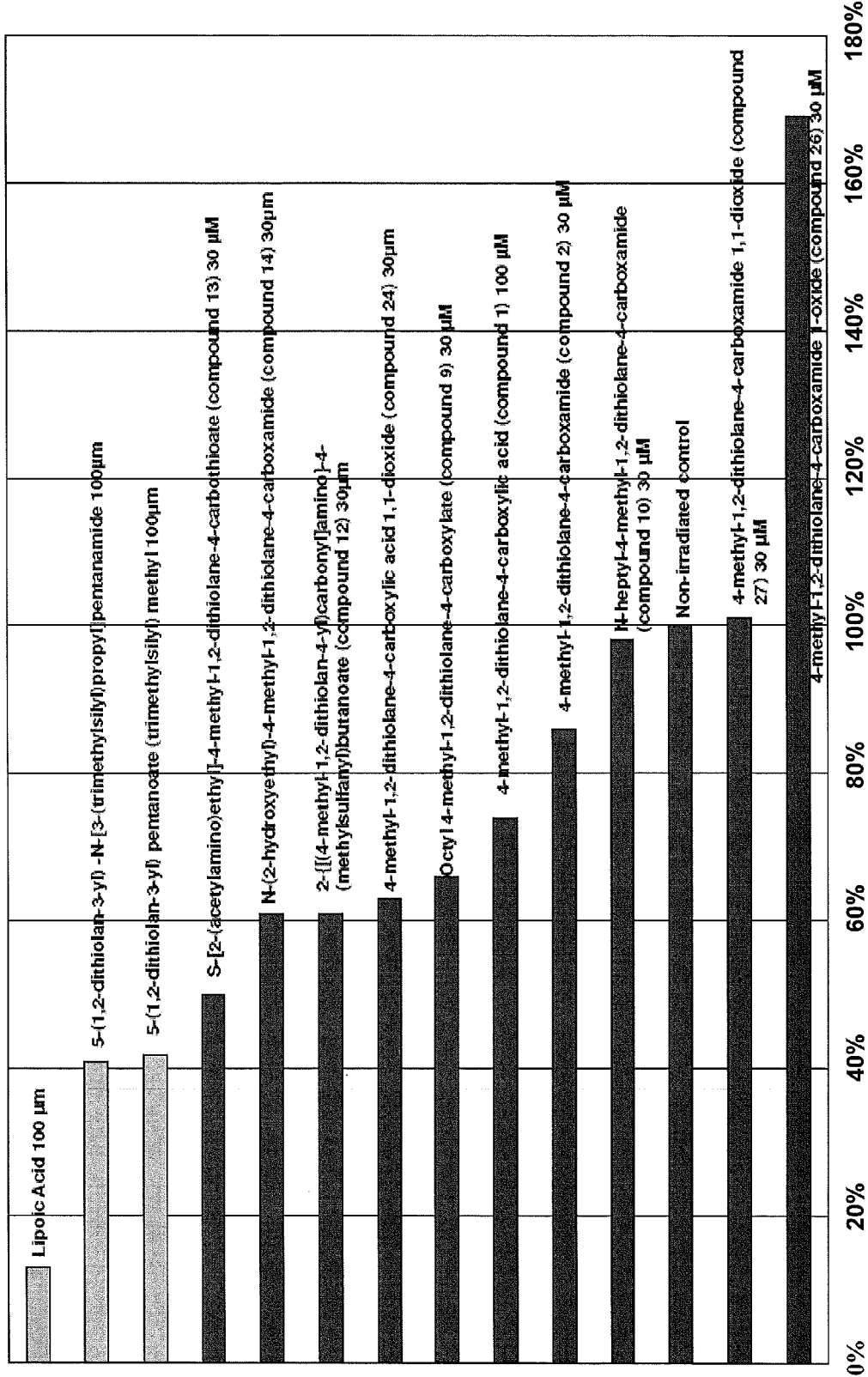

It is seen that the protection afforded by these active agents with respect to UV daylight-induced depletion of GSH is higher than that for the reference molecule, lipoic acid at 100 μM, this superiority occurring as low as 30 μM (see FIGS. 2 and 3).

Example 27

Measurement of the Protection Afforded with Respect to DNA Damage

Solar UV is capable of giving rise to extensive oxidative damage in skin cells, and especially in DNA. The nucleic acids absorb the UV-B photons, thus inducing DNA damage directly. Although UV-A is not directly absorbed by DNA, it has a genotoxic action mediated by reactive oxygen species. The comet test makes it possible to quantify the UV-induced DNA damage (in this case UV-A): the breaking of strands and oxidative DNA lesions (alkali-labile sites cleaved under alkaline conditions) are detected. The principle of this test is based on the capacity of denatured and cleaved DNA fragments to migrate outside the cell nuclei, under the influence of an electric field, whereas undamaged DNA remains confined in the nucleus. The damaged DNA fragments form a trail behind the cell nucleus. The cells then take the appearance of "comets". The "tail" of each comet is proportionately larger and stronger the greater the DNA damage incurred. (Alapetite C. et al., 1996, *Int. J. Rad. Bio.*; Klaude M, et al., 1996, *Mut. Res.*; Lehmann J. et al., 1998, *Mut. Res.*; Singh N P. et al., 1988, *Exp. Cell Res.*).

The study consisted in evaluating the photoprotective effect of two molecules with respect to UV-A-induced DNA damage. To do this, normal human fibroblasts (NHF) were placed in contact with the active agents for 24 hours. The cells were then detached, included in an agarose gel and then deposited on a microscope slide. Following the UV-A exposure (for 30 minutes), the cells were subjected to cell lysis (so as to keep intact only the genetic material), to a DNA-denaturing step and then to electrophoresis to make the damaged DNA migrate. The level of damaged DNA was measured using a fluorescence microscope combined with specialized image analysis software.

Pretreatment of the cells with compound 1 gives the fibroblasts a protection of 20% at 1 μM and 30% at 10 μM. Compound 2 was evaluated under the same conditions. It affords protection of 63% at 10 μM. These two compounds that have the capacity to protect against UV-induced DNA degradation.

| Evaluated active agents | Mean TM (DNA damage) | IC 95% | % of DNA damage | % protection |
|---|---|---|---|---|
| Compound 1 | | | | |
| Control (UV-A = 30 min) | 11.62 | 1.32 | 100 | 0 |
| 1 μM | 9.38 | 0.77 | 80.7 | 19.3 |
| 10 μM | 8.06 | 0.72 | 69.4 | 30.6 |
| Compound 2 | | | | |
| Control (UV-A = 30 min) | 7.37 | 0.44 | 100 | 0 |
| 10 μM | 2.73 | 0.18 | 37.1 | 62.9 |

Example 28

Anti-Sun Composition (Oil-In-Water Emulsion)

| | |
|---|---|
| Compound of Example 1, 2, 9, 10, 12, 13 or 14 | 3 g |
| 80/20 mixture of cetylstearyl alcohol and of oxyethylenated cetylstearyl alcohol (33 EO units) marketed by Tensia under the trademark Dehsconet ® 390 | 3 g |
| Glyceryl mono- and distearate mixture marketed under the trademark Cerasynth ® SD by ISP | 2 g |
| Cetyl alcohol | 1.5 g |
| Polydimethylsiloxane marketed under the trademark DC200 Fluid ® by Dow Corning | 1.5 g |
| Glycerol | 15 g |
| Parleam = hydrogenated isoparaffin (6-8 mol of isobutylene) by NOF Corporation | 20 g |
| Preservatives qs | |
| Demineralized water qs | 77 g |

The fatty phase containing the compound is heated at about 70°-80° C. until completely melted. The water is then added in a single portion at 80° C. with vigorous stirring. Stirring is continued for 10 to 15 minutes, the mixture is then allowed to cool with moderate stirring to about 40° C. and the preservatives are added.

Example 29

Anti-Sun Composition (Oil-In-Water Emulsion)

| | |
|---|---|
| Compound of Example 1, 2, 9, 10, 12, 13 or 14 | 2 g |
| 80/20 mixture of cetylstearyl alcohol and of oxyethylenated cetylstearyl alcohol (33 EO units) marketed by Tensia under the trademark Dehsconet ® 390 | 3 g |
| Glyceryl mono- and distearate mixture marketed under the trademark Cerasynth ® SD by ISP | 2 g |
| Cetyl alcohol | 2.5 g |
| $C_{12}$-$C_{15}$ alkyl benzoate marketed under the trademark Finsolv TN by Witco | 20 g |
| Polydimethylsiloxane marketed under the trademark DC200 Fluid ® by Dow Corning | 1.5 g |
| Glycerol | 15 g |
| Preservatives qs | |
| Demineralized water qs | 97 g |

This cream is prepared according to the standard techniques for preparing emulsions by dissolving the screening agent in the fatty phase containing the emulsifiers, heating this fatty phase to 70-80° C. and adding, with vigorous stirring, the water heated to the same temperature. Stirring is continued for 10 to 15 minutes and the mixture is then allowed to cool with moderate stirring, and the fragrance and preservative are finally added at about 40° C.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime or regimen for increasing the level of intracellular glutathione in a subject in need of such treatment, comprising administering thereto a thus effective amount of at least one dithiolane compound having the formula (I):

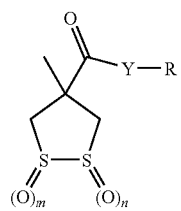

in which:

Y is O, $NR_1$ or S;

$R_1$ is a hydrogen atom, a saturated linear $C_1$-$C_{20}$ or branched $C_3$-$C_{20}$ or unsaturated $C_2$-$C_{20}$ alkyl hydrocarbon-based radical, a phenyl radical optionally substituted with one or more hydroxyl groups and/or with one or more $C_1$-$C_8$ alkoxy radicals;

R is a hydrogen atom, a saturated linear $C_1$-$C_{20}$ or branched $C_3$-$C_{20}$ or unsaturated $C_2$-$C_{20}$ alkyl hydrocarbon-based radical, a phenyl radical optionally substituted with one or more hydroxyl groups and/or with one or more $C_1$-$C_8$ alkoxy radicals, or a saturated $C_1$-$C_8$ alkyl radical containing a phenyl substituent optionally substituted with one or more hydroxyl groups and/or with one or more $C_1$-$C_8$ alkoxy radicals;

R optionally bears one or more substituents selected from among $OR_2$, $SR_2$, $NR_2R_3$ and $COOR_2$ in which:

$R_2$ is a hydrogen atom or a saturated linear $C_1$-$C_5$ or branched $C_3$-$C_5$ or unsaturated $C_2$-$C_5$ hydrocarbon-based radical, or a phenyl radical;

$R_3$ is a hydrogen atom, a saturated linear $C_1$-$C_5$ or branched $C_3$-$C_5$ or unsaturated $C_2$-$C_5$ hydrocarbon-based radical, a phenyl radical, or an acetyl radical, with the proviso that when Y is $NR_1$, R and $R_1$ may together form a ring member selected from among pyrrolidine, pyrroline, piperazine, morpholine, thiomorpholine and azepine;

m=0 or 1 or 2;

n=0 or 1 or 2;

and also the salts, chelates, and optical isomers thereof.

2. A regime or regimen for reinforcing and/or preserving the natural antioxidant protection of the skin against oxidative stress, comprising administering to a subject in need of such treatment, a thus effective amount of at least one dithiolane compound as defined in claim 1.

3. The regime or regimen as defined by claim 2, comprising reinforcing and/or preserving the natural antioxidant protection of the skin against oxidative stress caused by UV radiation.

4. The regime or regimen as defined by claim 1, said level of glutathione having been depleted by UV radiation.

5. A regime or regimen for reinforcing and/or preserving the endogenous system of antioxidant defense of the skin against oxidative stress caused by UV radiation, comprising administering to a subject in need of such treatment, a thus effective amount of at least one dithiolane compound as defined in claim 1.

6. A regime or regimen for reinforcing and/or preserving in a subject the level of endogenous intracellular glutathione that imparts to the skin natural antioxidant protection, comprising administering thereto a thus effective amount of at least one dithiolane compound as defined in claim 1.

7. A regime or regimen for treating UV stress and/or heating sensations caused by solar UV-A and/or UV-B radiation, comprising administering to a subject in need of such treatment, a thus effective amount of at least one dithiolane compounds as defined in claim 1.

8. A regime or regimen for treating skin and/or mucous membrane disorders induced by UV-A and/or UV-B irradiation, comprising administering to a subject in need of such treatment, a thus effective amount of at least one dithiolane compound as defined in claim 1.

9. A regime or regimen for treating DNA lesions caused by solar radiation and for preventing the development of skin cancers, comprising administering to a subject in need of such treatment, a thus effective amount of at least one dithiolane compound as defined in claim 1.

10. A regime or regimen for limiting the formation of free radicals and/or removing the free radicals present in skin cells, comprising administering to a subject in need of such treatment, a thus effective amount of at least one dithiolane compound as defined in claim 1.

11. A regime or regimen for treating the harmful effects of pollution on the skin, comprising administering to a subject in need of such treatment, a thus effective amount of at least one dithiolane compound as defined in claim 1.

12. A regime or regimen for limiting and/or eliminating the peroxidation of skin lipids, comprising administering to a subject in need of such treatment, a thus effective amount of at least one dithiolane compound as defined in claim 1.

13. The regime or regimen as defined by claim 1 or 2, wherein
formula (I):
Y is S, O or $NR_1$;
$R_1$ is a hydrogen atom, a saturated linear $C_1$-$C_{10}$ or branched $C_3$-$C_{10}$ alkyl hydrocarbon-based radical;
R is a hydrogen atom, a saturated linear $C_1$-$C_{20}$ or branched $C_3$-$C_{20}$ alkyl hydrocarbon-based radical, a phenyl radical optionally substituted with one or more hydroxyl groups and/or with one or more $C_1$-$C_3$ alkoxy radicals, a saturated $C_1$-$C_5$ alkyl radical bearing a phenyl substituent optionally substituted with one or more hydroxyl groups and/or with one or more $C_1$-$C_3$ alkoxy radicals, a linear $C_1$-$C_5$ alkyl hydrocarbon-based radical substituted with one or more identical or different radicals selected from $OR_2$, $SR_2$, $NR_2R_3$ and $COOR_2$ in which:
$R_2$ is a hydrogen atom or a saturated linear $C_1$-$C_5$ or branched $C_3$-$C_5$ or unsaturated $C_2$-$C_5$ hydrocarbon-based radical;
$R_3$ is a hydrogen atom, a saturated linear $C_1$-$C_5$ or branched $C_3$-$C_5$ hydrocarbon-based radical; a phenyl radical, an acetyl radical;
with the proviso that when Y=$NR_1$, R and $R_1$ may together form a pyrrolidine ring;
n=0 or 1 or 2;
m=0 or 1 or 2;
and also the acid or base salts, chelates, and optical isomers thereof.

14. The regime or regimen as defined by claim 1 or 2, wherein
formula (I):
Y is O or $NR_1$;
$R_1$ is a hydrogen atom, a saturated linear $C_1$-$C_{10}$ or branched $C_3$-$C_{10}$ alkyl hydrocarbon-based radical;
R is a hydrogen atom, a saturated linear $C_1$-$C_{10}$ or branched $C_3$-$C_{10}$ alkyl hydrocarbon-based radical, a phenyl radical optionally substituted with one or more hydroxyl groups and/or with one or more methoxy radicals, a saturated $C_1$-$C_3$ alkyl hydrocarbon-based radical bearing a phenyl substituent optionally substituted with one or more hydroxyl groups and/or with one or more methoxy radicals, a linear $C_1$-$C_4$ alkyl hydrocarbon-based radical substituted with one or more identical or different radicals selected from among $OR_2$, $SR_2$, $NR_2R_3$ and $COOR_2$ in which:
$R_2$ is a hydrogen atom or a saturated linear $C_1$-$C_5$ or branched $C_3$-$C_5$ hydrocarbon-based radical;
$R_3$ is a hydrogen atom, a saturated linear $C_1$-$C_5$ or branched $C_3$-$C_5$ hydrocarbon-based radical;
n=0 or 1 or 2;
m=0 or 1 or 2;
and also the acid or base salts, chelates, and optical isomers thereof.

15. The regime or regimen as defined by claim 1 or 2, wherein formula (I):
Y is $NR_1$;
$R_1$ is a hydrogen atom, a saturated linear $C_1$-$C_4$ alkyl hydrocarbon-based radical;
R is a hydrogen atom, a saturated linear $C_1$-$C_{10}$ or branched $C_3$-$C_{10}$ alkyl hydrocarbon-based radical, a phenyl radical, a saturated linear $C_1$-$C_4$ alkyl radical substituted with a phenyl radical optionally substituted with one or more identical or different groups selected from OH and OMe, a linear $C_1$-$C_4$ alkyl hydrocarbon-based radical substituted with one or more identical or different radicals selected from among OH, NHAc, $SR_2$ and $COOR_2$ wherein $R_2$ is a hydrogen atom or a linear $C_1$-$C_4$ alkyl radical;
n=0 or 1 or 2, m=0 or 1 or 2;
and also the acid or base salts, chelates, solvates and optical isomers thereof.

16. The regime or regimen as defined by claim 1 or 2, wherein formula (I):
Y is NH;
R is a hydrogen atom, a saturated linear $C_1$-$C_{10}$ or branched $C_3$-$C_{10}$ alkyl hydrocarbon-based radical, a phenyl radical, a saturated linear $C_1$-$C_4$ alkyl radical substituted with a phenyl radical optionally substituted with one or more identical or different groups selected from OH and OMe, a linear $C_1$-$C_4$ alkyl hydrocarbon-based radical substituted with one or more identical or different radicals selected from among OH, NHAc, $SR_2$ and $COOR_2$ wherein $R_2$ is a hydrogen atom or a linear $C_1$-$C_4$ alkyl radical;
n=0 or 1 or 2;
m=0 or 1 or 2;
and also the acid or base salts, chelates, solvates and optical isomers thereof.

17. The regime or regimen as defined by claim 1 or 2, wherein formula (I):
Y is NH;
R is a hydrogen atom, a saturated linear $C_1$-$C_{10}$ or branched $C_3$-$C_{10}$ alkyl hydrocarbon-based radical;
n=0 or 1 or 2;
m=0 or 1 or 2;
and also the acid or base salts, chelates, solvates and optical isomers thereof.

18. The regime or regimen as defined by claim 1 or 2, wherein said at least one dithiolane compound is/are selected from the group consisting of:

| No. | Structure | Chemical name |
|---|---|---|
| 1. | ![structure with CO2H and S-S ring] | 4-methyl-1,2-dithiolane-4-carboxylic acid |

-continued
| No. | Structure | Chemical name |
|---|---|---|
| 2. | 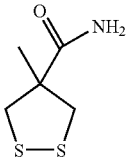 | 4-methyl-1,2-dithiolane-4-carboxamide |
| 3. | 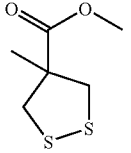 | methyl 4-methyl-1,2-dithiolane-4-carboxylate |
| 4. | 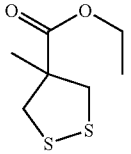 | ethyl 4-methyl-1,2-dithiolane-4-carboxylate |
| 5. | 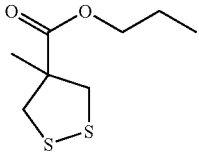 | propyl 4-methyl-1,2-dithiolane-4-carboxylate |
| 6. | 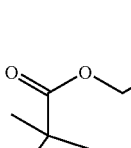 | benzyl 4-methyl-1,2-dithiolane-4-carboxylate |
| 7. | 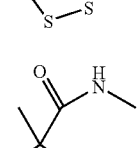 | N-methyl-4-methyl-1,2-dithiolane-4-carboxamide |
| 8. | 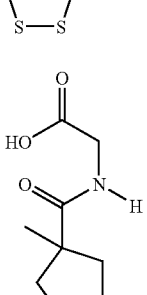 | {[(4-methyl-1,2-dithiolan-4-yl)carbonyl]amino}acetic acid |
| 9. | 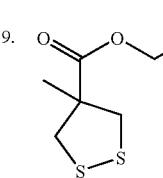 | octyl 4-methyl-1,2-dithiolane-4-carboxylate |

-continued

| No. | Structure | Chemical name |
|---|---|---|
| 10. | 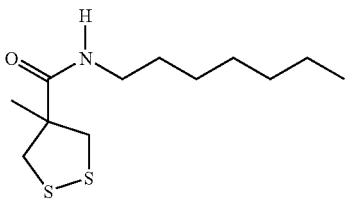 [SMILES: CCCCCCCNC(=O)C1(C)CSSC1] | N-heptyl-4-methyl-1,2-dithiolane-4-carboxamide |
| 11. | 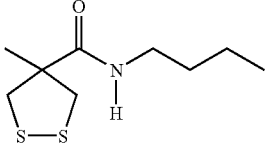 | N-butyl-4-methyl-1,2-dithiolane-4-carboxamide |
| 12. | 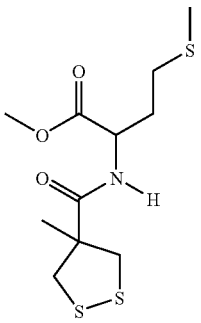 | methyl 2-{[(4-methyl-1,2-dithiolan-4-yl)carbonyl]amino}-4-(methylsulfanyl)butanoate |
| 13. | 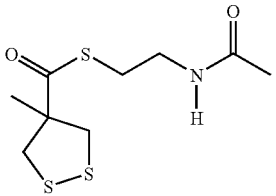 | S-[2-(acetylamino)ethyl] 4-methyl-1,2-dithiolane-4-carbothioate |
| 14. | 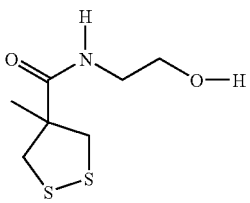 | N-(2-hydroxyethyl)-4-methyl-1,2-dithiolane-4-carboxamide |
| 15. | 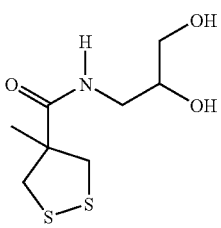 | N-(2,3-dihydroxypropyl)-4-methyl-1,2-dithiolane-4-carboxamide |
| 16. | 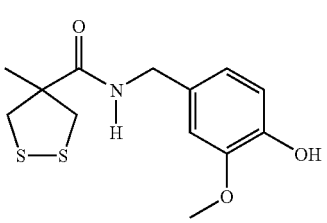 [SMILES: COc1cc(CNC(=O)C2(C)CSSC2)ccc1O] | N-(4-hydroxy-3-methoxybenzyl)-4-methyl-1,2-dithiolane-4-carboxamide |

| No. | Structure | Chemical name |
|---|---|---|
| 17. | 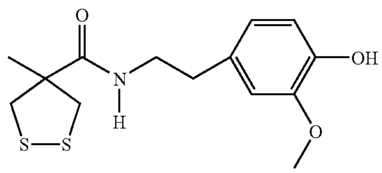 [SMILES: COc1cc(CCNC(=O)C2(C)CSSC2)ccc1O] | N-[2-(4-hydroxy-3-methoxyphenyl)ethyl]-4-methyl-1,2-dithiolane-4-carboxamide |
| 18. | 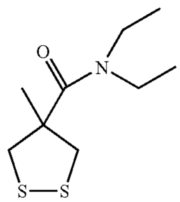 | N,N-diethyl-4-methyl-1,2-dithiolane-4-carboxamide |
| 19. | 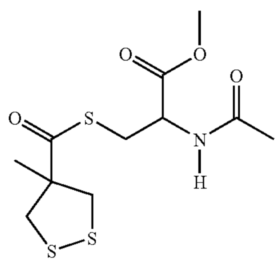 [SMILES: COC(=O)C(CSC(=O)C1(C)CSSC1)NC(C)=O] | methyl 2-(acetylamino)-3-{[(4-methyl-1,2-dithiolan-4-yl)carbonyl]sulfanyl}propanoate |
| 20. | 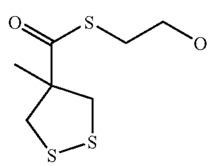 | S-(2-hydroxyethyl) 4-methyl-1,2-dithiolane-4-carbothioate |
| 21. | 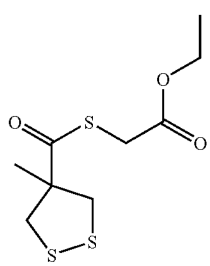 | ethyl {[(4-methyl-1,2-dithiolan-4-yl)carbonyl]sulfanyl}acetate |
| 22. | 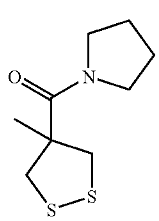 | [(4-methyl-1,2-dithiolan-4-yl)carbonyl]pyrrolidine |
| 23. | 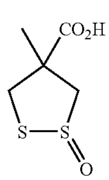 | 4-methyl-1,2-dithiolane-4-carboxylic acid 1-oxide |

-continued

| No. | Structure | Chemical name |
|---|---|---|
| 24. | 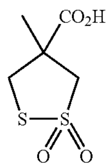 | 4-methyl-1,2-dithiolane-4-carboxylic acid 1,1-dioxide |
| 25. | 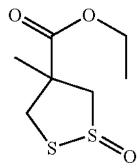 | ethyl 4-methyl-1,2-dithiolane-4-carboxylate 1-oxide |
| 26. | 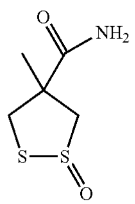 | 4-methyl-1,2-dithiolane-4-carboxamide 1-oxide |
| 27. | 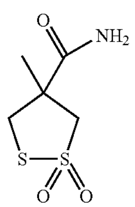 | 4-methyl-1,2-dithiolane-4-carboxamide 1,1-dioxide |
| 28. | 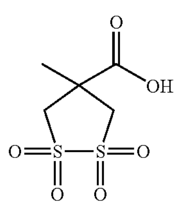 | 4-methyl-1,2-dithiolane-4-carboxylic acid 1,1,2,2-tetroxide |
| 29. | 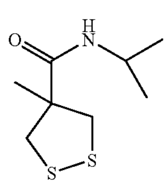 | 4-methyl-N-(1-methylethyl)-1,2-dithiolane-4-carboxamide |
| 30. | 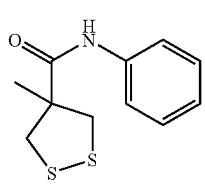 | 4-methyl-N-phenyl-1,2-dithiolane-4-carboxamide |
| 31. | 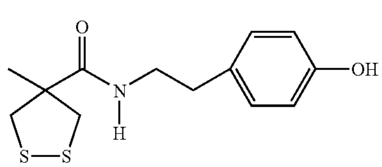 [SMILES: CC1(C(=O)NCCc2ccc(O)cc2)CSSC1] | N-[2-(4-hydroxyphenyl)ethyl]-4-methyl-1,2-dithiolane-4-carboxamide |

-continued

| No. | Structure | Chemical name |
|---|---|---|
| 32. | 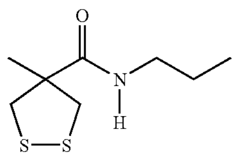 | N-propyl-4-methyl-1,2-dithiolane-4-carboxamide |
| 33. | 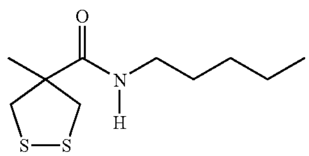 | N-pentyl-4-methyl-1,2-dithiolane-4-carboxamide |
| 34. | 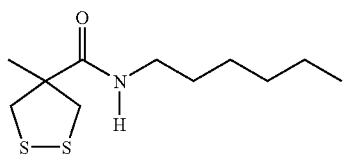 | N-hexyl-4-methyl-1,2-dithiolane-4-carboxamide |
| 35. | 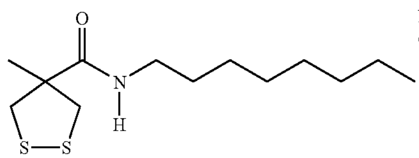 | N-octyl-4-methyl-1,2-dithiolane-4-carboxamide |
| 36. | 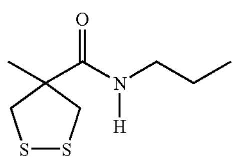 | N-propyl-4-methyl-1,2-dithiolane-4-carboxamide |
| 37. | 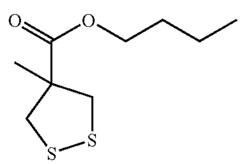 | butyl 4-methyl-1,2-dithiolane-4-carboxylate |
| 38. | 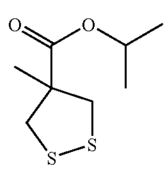 | isopropyl 4-methyl-1,2-dithiolane-4-carboxylate |
| 39. | 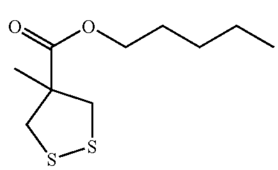 | pentyl 4-methyl-1,2-dithiolane-4-carboxylate |
| 40. | 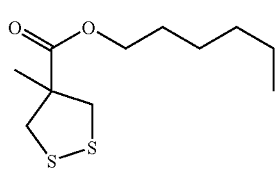 | hexyl 4-methyl-1,2-dithiolane-4-carboxylate |

| No. | Structure | Chemical name |
|---|---|---|
| 41. | 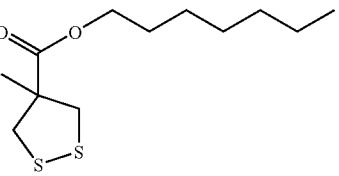 | heptyl 4-methyl-1,2-dithiolane-4-carboxylate. |

19. The regime or regimen as defined by claim 1 or 2, wherein said at least one dithiolane compound is/are selected from the group consisting of:

| No. | Structure | Chemical name |
|---|---|---|
| 1. | 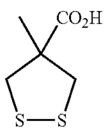 | 4-methyl-1,2-dithiolane-4-carboxylic acid |
| 2. | 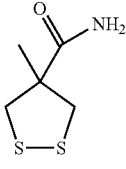 | 4-methyl-1,2-dithiolane-4-carboxamide |
| 9. | 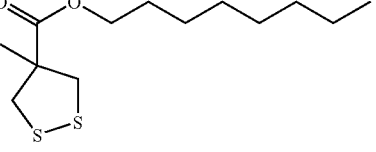 | octyl 4-methyl-1,2-dithiolane-4-carboxylate |
| 10. | 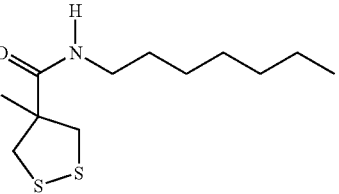 | N-heptyl-4-methyl-1,2-dithiolane-4-carboxamide |
| 26. | 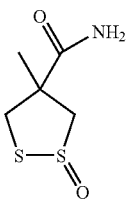 | 4-methyl-1,2-dithiolane-4-carboxamide 1-oxide and |
| 27. | 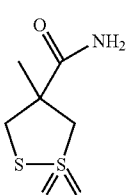 | 4-methyl-1,2-dithiolane-4-carboxamide 1,1-dioxide. |

* * * * *